US008987206B2

(12) United States Patent
Epshtein

(10) Patent No.: US 8,987,206 B2
(45) Date of Patent: *Mar. 24, 2015

(54) METHOD OF TREATING ATTENTION DEFICIT HYPERACTIVITY DISORDER

(76) Inventor: Oleg Iliich Epshtein, Moscow (RU)

(*) Notice: Subject to any disclaimer, the term of this patent is extended or adjusted under 35 U.S.C. 154(b) by 0 days.

This patent is subject to a terminal disclaimer.

(21) Appl. No.: 13/135,895

(22) Filed: Jul. 15, 2011

(65) Prior Publication Data
US 2012/0321672 A1 Dec. 20, 2012

(30) Foreign Application Priority Data

Jul. 21, 2010 (RU) .................................. 2010130358
Jul. 1, 2011 (RU) .................................. 2011127055

(51) Int. Cl.
A01N 37/18 (2006.01)
A61K 38/00 (2006.01)
A61K 39/395 (2006.01)
C07K 16/18 (2006.01)
A61K 41/00 (2006.01)
C07K 16/40 (2006.01)
A61K 39/00 (2006.01)

(52) U.S. Cl.
CPC ............ C07K 16/18 (2013.01); A61K 41/0004 (2013.01); A61K 2039/507 (2013.01); C07K 16/40 (2013.01)
USPC ...... 514/17.5; 514/17.6; 514/17.7; 424/130.1

(58) Field of Classification Search
None
See application file for complete search history.

(56) References Cited

U.S. PATENT DOCUMENTS

| | | |
|---|---|---|
| 3,901,967 A | 8/1975 | Cohen et al. |
| 4,963,367 A | 10/1990 | Ecanow |
| 5,683,712 A | 11/1997 | Cavazza |
| 5,846,514 A | 12/1998 | Foster et al. |
| 5,849,528 A | 12/1998 | Hillman et al. |
| 5,879,677 A | 3/1999 | del Zoppo |
| 5,895,783 A | 4/1999 | Garfield et al. |
| 6,150,500 A | 11/2000 | Salerno |
| 6,326,360 B1 | 12/2001 | Kanazawa et al. |
| 6,750,197 B1 | 6/2004 | Salerno |
| 7,396,659 B2 | 7/2008 | Singh |
| 7,572,441 B2 | 8/2009 | Epshtein et al. |
| 7,582,294 B2 | 9/2009 | Epshtein et al. |
| 7,700,096 B2 | 4/2010 | Epshtein et al. |
| 7,815,904 B2 | 10/2010 | Epshtein et al. |
| 7,923,009 B2 | 4/2011 | Epshtein et al. |
| 8,066,992 B2 | 11/2011 | Epshtein |
| 8,168,182 B2 | 5/2012 | Epshtein |
| 8,178,498 B1 | 5/2012 | Ephstein |
| 8,241,625 B2 | 8/2012 | Epshtein et al. |
| 8,524,229 B2 | 9/2013 | Epshtein et al. |
| 8,535,664 B2 | 9/2013 | Epshtein et al. |
| 8,617,555 B2 | 12/2013 | Epshtein |
| 8,637,030 B2 | 1/2014 | Epshtein |
| 8,637,034 B2 | 1/2014 | Epshtein |
| 2006/0153845 A1 | 7/2006 | Epshtein et al. |
| 2007/0123518 A1 | 5/2007 | Epshtein |
| 2007/0141058 A1 | 6/2007 | Iliich et al. |
| 2008/0025985 A1 | 1/2008 | Iliich et al. |
| 2008/0050360 A1 | 2/2008 | Iliich et al. |
| 2008/0050392 A1 | 2/2008 | Iliich et al. |
| 2008/0131440 A1 | 6/2008 | Epshtein et al. |
| 2009/0148521 A1 | 6/2009 | Epstehin |
| 2010/0166762 A1 | 7/2010 | Epshtein |
| 2010/0203059 A1 | 8/2010 | Epshtein |
| 2010/0221258 A1 | 9/2010 | Epshtein |
| 2010/0239569 A1 | 9/2010 | Epshtein |
| 2011/0008452 A1 | 1/2011 | Epshtein et al. |
| 2011/0086037 A1 | 4/2011 | Iliich |
| 2012/0045445 A1 | 2/2012 | Epshtein |
| 2012/0225074 A1 | 9/2012 | Epshtein et al. |
| 2012/0251584 A1 | 10/2012 | Epshtein et al. |
| 2012/0258146 A1 | 10/2012 | Epshtein |
| 2012/0263725 A1 | 10/2012 | Epshtein et al. |
| 2012/0263726 A1 | 10/2012 | Epshtein et al. |
| 2012/0294899 A1 | 11/2012 | Epshtein et al. |
| 2012/0321672 A1 | 12/2012 | Epshtein |
| 2013/0017202 A1 | 1/2013 | Epshtein et al. |
| 2013/0045237 A1 | 2/2013 | Epshtein et al. |
| 2013/0058981 A1 | 3/2013 | Epshtein |
| 2013/0058982 A1 | 3/2013 | Epshtein |
| 2013/0064860 A1 | 3/2013 | Epshtein |
| 2013/0171161 A1 | 7/2013 | Epshtein et al. |
| 2013/0189707 A1 | 7/2013 | Sergeeva et al. |

(Continued)

FOREIGN PATENT DOCUMENTS

| | | |
|---|---|---|
| EP | 0687466 A1 | 12/1995 |
| EP | 0884042 A1 | 12/1998 |

(Continued)

OTHER PUBLICATIONS

Castagne V., et al., "Antibodies to S100 Proteins have Anxiolytic-Like Activity at Ultra-Low Doses in the Adult Rat", J Pharm Pharmacol., 2008, vol. 60, No. 3, pp. 309-319.
Vyatcheslav. et al., "Antibodies to Calcium-Binding S100B Protein Block the Conditioning of Long-Term Sensitization in the Terrestrial Snail", Pharmacol Biochem Behay, 2009, vol. 94, No. 1, pp. 37-42.
Schwab., "Homeopathic Medicines", 1967, Moscow, pp. 1-37.
Frimel, "Immunologicheskie metody (Immunological Methods)", Moscow: Meditsina, 1987, p. 9-33.
Laffly E., et al., "Monoclonal and Recombinant Antibodies, 30 Years After", Human Antibodies, 2005, vol. 14, N. 1-2, pp. 33-55.

(Continued)

Primary Examiner — Olga N Chernyshev
(74) Attorney, Agent, or Firm — Pergament Gilman & Cepeda LLP

(57) ABSTRACT

The present invention relates to a method of treating attention deficit hyperactivity disorder (ADHD) and attention deficit disorder (ADD) by administration of activated-potentiate form of antibodies to brain-specific protein S-100 and activated-potentiate form of antibodies to endothelial NO synthase.

32 Claims, 1 Drawing Sheet

(56) References Cited

U.S. PATENT DOCUMENTS

| | | |
|---|---|---|
| 2013/0224219 A1 | 8/2013 | Epshtein et al. |
| 2013/0302312 A1 | 11/2013 | Epshtein et al. |
| 2013/0303735 A1 | 11/2013 | Epshtein et al. |
| 2013/0315964 A1 | 11/2013 | Epshtein et al. |
| 2013/0336985 A1 | 12/2013 | Epshtein et al. |
| 2014/0010819 A1 | 1/2014 | Epshtein et al. |
| 2014/0056923 A9 | 2/2014 | Epshtein et al. |
| 2014/0112934 A1 | 4/2014 | Epshtein |

FOREIGN PATENT DOCUMENTS

| | | |
|---|---|---|
| EP | 1466622 A1 | 10/2004 |
| EP | 1547612 A1 | 6/2005 |
| RU | 2007989 C1 | 2/1994 |
| RU | 2033784 C1 | 4/1995 |
| RU | 2104032 C1 | 2/1998 |
| RU | 2156621 C1 | 9/2000 |
| RU | 2187334 C2 | 8/2002 |
| RU | 2192882 C1 | 11/2002 |
| WO | 9728776 A1 | 8/1997 |
| WO | 9814161 A1 | 4/1998 |
| WO | 9814166 A1 | 4/1998 |
| WO | 0105371 A1 | 1/2001 |

OTHER PUBLICATIONS

Epshtein, et al., "Effect of Potentiated Antibodies to Brain-Specific Protein S100 on the Integrative Avtivity of the Brain", Bulletin of Experimental Biology and Medicine, 1999, vol. 127, Issue 5, pp. 493-495.
Marsden, et al., "Molecular Cloning and Characterization of Human Endothelial Nitric Oxide Synthase", FEBS, Aug. 1992, vol. 307, No. 3, pp. 287-293.
Bin, et al., "Inhibition of S100A11 Gene Expression Impairs Keratinocyte Response Against Vaccinia Virus Through Downregulation of the IL-10 Receptor 2 Chain", J Allergy Clin Immunol, Aug. 2009, vol. 124, No. 2, pp. 270-277.e1.
Hu, et al., "S100B Induces Normal Cell Death Through Nitric Oxide Release from Astrocytes", Journal of Neurochemistry, 1997, vol. 69, pp. 2294-2301.
Wiencken, et al., "Endothelial Nitric Oxide Synthetase (eNOS) in Astrocytes: Another Source of Nitric Oxide in Neocortex", GLIA, 1999, vol. 26, pp. 280-290.
Zhavbert E.S., et al., "Evaluation of the Efficiency and Safety of Combined Treatment with Impaza and Nitrates in CHD Patients with Erectile Dysfunction", 2009, Bulletin of Experimental Biology and Medicine, vol. 148, Suppl. 1, pp. 325-327.
Beregovoy, et al., "On Influence of Various Dilutions of Monoclonal Antibodies 5F5B6 on the Formation of Long-Term Post-Tetanic Potentiation in Survived Hippocampal Slices", Bulletin of Siberian Branch of RAMS, 1999, No. 1, pp. 91-96.
Dugina, et al., "Anti-S100 Antibodies Modulate Locomotor Activity and Exploratory Behaviour of Immature Rats", European Neuropsychopharmacology, Oct. 1, 2007, vol. 17, p. S571.
Borovskaya T.G., "Impact of Antibodies to Endothelial NO-Synthase on Sexual Behavior of Male Rats in Conditions of Seasonal Suppression of Reproductive Function", Biull Eksp Biol Med, 2001, p. 52-53, ISSN 0365-9615. (Russian).
Borovskaya T.G., "Impact of Antibodies to Endothelial NO-Synthase on Sexual Behavior of Male Rats in Conditions of Seasonal Suppression of Reproductive Function", Scientific-Research Institute of Pharmacology 2001, Moscow. (English Translation).
Davenas E., "Human Basophil Degranulation Triggered by Very Dilute Antiserum Against IgE", Nature, Jun. 30, 1988, vol. 333, p. 816-818.
Goldacre, "Benefits and Risks of Homoeopathy", The Lancet, Nov. 17, 2007, vol. 370, p. 1672-1673.
Pavlov I. F., "Effects of Antibodies Against S-100 Antigen in Ultralow Doses (Proproten-100) on Acquisition of Avoidance Response in Rats", Bulletin of Experimental Biology and Medicine, 2004, vol. 138, Issue 6, p. 556-558.
Epshtein O. I., et al., "Effects of Homeopathic Doses of Antibodies to S100 Antigen on Electric Characteristics of Neuronal Membranes", Bulletin of Experimental Biology and Medicine, 1999, vol. 127, Issue 4, p. 423-424.
Epshtein O. I., et al., "Improvement of Memory by Means of Ultra-Low Doses of Antibodies to S-100B Antigen", ECAM, 2006, vol. 3, No. 4, p. 541-545.
Epshtein O. I., et al., "Effects of Potentiated Antibodies to Brain Specific Protein S100 on the Dynamics of Long-Term Potentiation in Hippocampal Slices", Bulletin of Experimental Biology and Medicine, Mar. 1999, vol. 127, Issue 3, p. 286-289.
Epshtein O. I., "Regulatrory Activity of Ultralow Doses", Bulletin of Experimental Biology and Medicine, 2003, vol. 135, Issue 7 Supplement, p. 8-13.
Voronina T. A., "Effect of Ultralow Doses of Antibodies to S-100 Protein in Animals with Impaired Cognitive Function and Disturbed Emotional and Neurological Status under Conditions of Experimental Alzheimer Disease", Bulletin of Experimental Biology and Medicine, Sep. 2009, vol. 148, Issue 3, p. 533-535.
Enserink, "French Nobelist Escapes "Intellectual Terror" to Pursue Radical Ideas in China", Science, Dec. 24, 2010, vol. 330, No. 6012, p. 1732.
Hyman, et al., "National Institute on Aging-Alzheimer's Association Guidelines for the Neuropathologic Assessment of Alzheimer's Disease", Alzheimer's & Dementia, 2012, vol. 8, p. 1-13.
Shang A et al: "Are the clinical effects of homoeopathy placebo effects? Comparative study of placebo-controlled trials of homoeopathy and allopathy", The Lancet, Lancet Limited. London, GB, vol. 366, No. 9487, Aug. 27, 2005, pp. 726-732.
T. A. Voronina et al: "Study of the Effects of Preparation Containing Ultralow Doses of Antibodies to S-100 Protein in Experimental Hemorrhagic Stroke", Bulletin of Experimental Biology and Medicine, vol. 148, No. 3, Sep. 1, 2009, pp. 530-532.
Jonas Wayne B et al: "A critical overview of homeopathy", Annals of Internal Medicine, New York, NY; US, US, vol. 138, No. 5, Mar. 4, 2003 pp. 393-399.
Vickers A J: "Clinical Trials of Homeopathy and Placebo: Analysis of a Scientific Debate", Journal of Alternative and Complementary Medicine, Mary Ann Liebert, New York, NY, US, vol. 6, No. 1, Feb. 1, 2000, pp. 49-56.
Romanova G A et al: "Neuroprotective Activity of Proproten in Rats with Experimental Local Photothrombosis of the Prefrontal Cortex", Bulletin of Experimental Biology and Medicine, Kluwer Academic Publishers-Plenum Publishers, NE, vol. 139, No. 4, Apr. 1, 2005, pp. 404-407.
Epstein 0 I et al: "Psychotropic drug tenoten activates mitogen-activated MAP/ERK kinase regulatory cascade controlling the neuroprotective effects", Bulletin of Experimental Biology and Medicine, Kluwer Academic Publishers-Plenum Publishers, NE, vol. 144, No. 3, Sep. 1, 2007, pp. 319-321.
Notification of Transmittal of International Search Report and Written Opinion dated Feb. 29, 2012 for corresponding International Patent Application No. PCT/IB2011/002364.
International Search Report dated Feb. 29, 2012 for corresponding International Patent Application No. PCT/IB2011/002364.
Faraci, "Protecting the brain with eNOS: Run for your life", Circ Res. 2006:99 1029-1030.
Yardan, et al. "Usefulness of S100B Protein in Neurological Disorders". J Pak Med Assoc, vol. 61, No. 3, Mar. 2011, 276-281.
Linde, et al., "Are the clinical effects of homeopathy placebo effects", A meta-analysis of placebo-controlled trials. Lancet 1997: 350: 834-843.
Ernst, Homeopathy: what does the "best" evidence tell us ? MJA vol. 192, No. 8, Apr. 19, 2010.
House of Commons Science and Technology Committe, Evidence Check 2: Homeopathy, Fourth Report of Session, 2009-2010.
Bombeiro, et al., Neurodegeneration and Increased Production of Nitroyyrosine, Nitric Oxide Synthase, IFN gama and S100 beta Protein in the Spinal Cord of IL-12p40-Deficient Mice Infected with *Trypanosoma cruzi*. Neuroimmunomodulation 2010; 17:67-78.
Janeway, et al., "Immunobiology: the Immune System in Health and Disease", 5th ed. 2001, Chapter 3.

(56) References Cited

OTHER PUBLICATIONS

Rohde, et al., "S100A1: A Multifaceted Therapeutic Target in Cardiovascular Disease". J. of Cardiovas. Trans. Res. (2010) 3: 525-537.

Spinazzola, et al., "Modular structure of awareness for sensorimotor disorders: Evidence from anosognosia for hemiplegia and anosognosia for hemianaesthesia", Neuropsychologia 46, (2008) 915-926.

Currey, et al., "Significance and importance: some common misapprehensions about statistics", Cell Biochem Funct 2009: 27: 499-502.

Linde, et al., "Impact of Study Quality on Outcome in Placebo-Controlled Trials of Homeopathy". J. Clin. Epidemiol, vol. 52, No. 7, pp. 631-636, 1999.

Written Opinion of the International Preliminary Examining Authority for corresponding International Patent Application No. PCT/IB2011/002327, dated Jul. 18, 2012.

International Preliminary Report on Patentability for corresponding International Patent Application No. PCT/IB2011/002327, dated Oct. 17, 2012.

Enserink, "French Nobelist Escapes 'Intellectual Terror' to Pursue Radical Ideas in China", Science, vol. 330, No. 6012, Dec. 24, 2010, p. 1732.

Kirkby, et al, "Homeopathic trial design in influenza treatment", Homeopathy, Chuchill Livingstone, Amsterdam, NL, vol. 99, No. 1, Jan. 1, 2010, pp. 69-75. XP026988523.

Kheyfets I et al: "P01-219—Clinical efficacy of tenoten for children in treatment of attention deficit and hyperactivity disorder", European Psychiatry, Editions Scientifiques Et Medicales Elsevier, FR, vol. 25, No. Supplement 1, Jun. 7, 2010.

Dugina et al: "P.7.b.004 Anti-S100 antibodies modulate locomotor activity and exploratory behaviour of immature rats", European Neuropsychopharmacology, Elsevier Science Publishers BV, Amsterdam, NL, vol. 17, Oct. 1, 2007, p. S571.

Notification of Transmittal of International Search Report and Written Opinion dated Feb. 29, 2012 for corresponding International Patent Application No. PCT/IB2011/002327.

International Search Report dated Feb. 29, 2012 for corresponding International Patent Application No. PCT/IB2011/002327.

Written Opinion of the International Searching Authority for corresponding International Patent Application No. PCT/IB2011/002327, 2012.

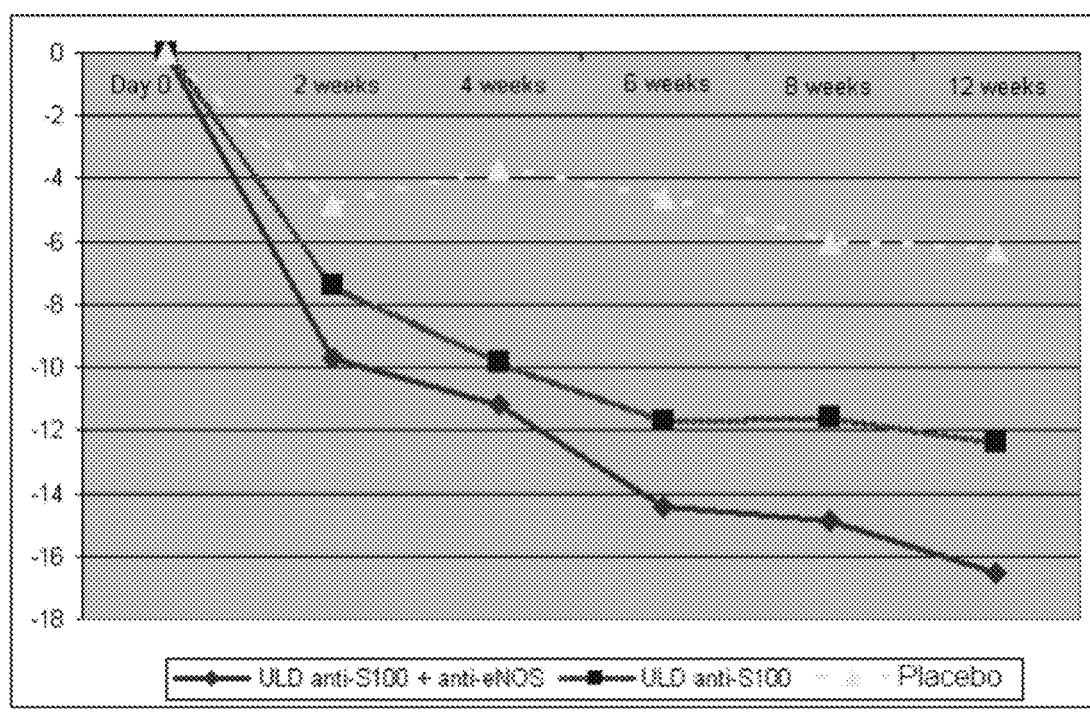

METHOD OF TREATING ATTENTION DEFICIT HYPERACTIVITY DISORDER

FIELD

The present invention relates to the field of medicine and can be used for the treatment of attention deficit hyperactivity disorder.

BACKGROUND

Attention deficit hyperactivity disorder (ADHD) is one of the most frequent neurobehavioral diseases of children's age and is observed in 4-10% of children. Approximately in 50% of children diagnosed with ADHD have symptoms that persist into adulthood. Emotional restlessness, impulsive behavior and thought, lack of attention, inability to concentrate and focus, talking excessively, absent-mindedness, etc. are some of the symptoms of ADHD.

Neurotropic drugs having antiserum to brain-specific protein S-100 are known. (RU 2156621 C1, A61K39/395, Sep. 27, 2000). However, these medicines do not provide sufficient therapeutic efficiency for treatment of neurobehavioral diseases, including attention deficit hyperactivity disorder. Thus, there is a continuing need for new drug products with the desired therapeutic efficacy for the treatment of attention deficit hyperactivity disorder.

The therapeutic effect of an extremely diluted form (or ultra-low form) of antibodies potentized by homeopathic technology (activated-potentiated form) has been discovered by the inventor of the present patent application, Dr. Oleg I. Epshtein. U.S. Pat. No. 7,582,294 discloses a medicament for treating Benign Prostatic Hyperplasia or prostatitis by administration of a homeopathically activated form of antibodies to prostate specific antigen (PSA). U.S. Pat. No. 7,700,096 discloses a homeopathically potentized form of antibodies to endothelial NO-synthase.

The S-100 protein is a cytoplasmic acidic calcium binding protein found predominantly in the gray matter of the brain, primarily in glia and Schwann cells. The protein exists in several homo- or heterodimeric isoforms consisting of two immunologically distinct subunits, alpha and beta. The S-100 protein has been suggested for use as an aid in the diagnosis and assessment of brain lesions and neurological damage due to brain injury, as in stroke. Yardan et al., *Usefulness of S100B Protein in Neurological Disorders*, J Pak Med Assoc Vol. 61, No. 3, March 2011, which is incorporated herein by reference.

Ultra-low doses of antibodies to S-100 protein have been shown to have anxiolytic, anti-asthenic, anti-aggressive, stress-protective, anti-hypoxic, anti-ischemic, neuroprotective and nootropic activity. See Castagne V. et al., *Antibodies to S100 proteins have anxiolytic-like activity at ultra-low doses in the adult rat*, J Pharm Pharmacol. 2008, 60(3):309-16; Epstein O. I., *Antibodies to calcium-binding S100B protein block the conditioning of long-term sensitization in the terrestrial snail*, Pharmacol Biochem Behav., 2009, 94(1): 37-42; Voronina T. A. et al., Chapter 8. *Antibodies to S-100 protein in anxiety-depressive disorders in experimental and clinical conditions*. In "Animal models in biological psychiatry", Ed. Kalueff A. V. NY, "Nova Science Publishers, Inc.", 2006, pp. 137-152, all of which are incorporated herein by reference.

Nitric oxide (NO) is a gaseous molecule that has been shown to acts in the signaling of different biological processes. Endothelium-derived NO is a key molecule in regulation of vascular tone and its association with vascular disease has long been recognized. NO inhibits many processes known to be involved in the formation of atherosclerotic plaque, including monocyte adhesion, platelet aggregation and vascular smooth muscle cell proliferation. Another important role of endothelial NO is the protection of the vascular wall from the oxidative stress induced by its own metabolic products and by the oxidation products of lipids and lipoproteins. Endothelial dysfunction occurs at very early stages of atherosclerosis. It is therefore possible that deficiency in local NO availability could be a final common pathway that accelerates atherogenesis in humans. In addition to its role in the vascular endothelium, NO availability has been shown to modulate metabolism of lipoproteins. Negative correlation has been reported between plasma concentrations of NO metabolic products and plasma total and Low Density Lipoprotein [LDL] cholesterol levels while High Density Lipoprotein [HDL] improves vascular function in hypercholesterolaemic subjects. The loss of NO has considerable effect on the development of the disease. Diabetes mellitus is associated with increased rates of morbidity and mortality caused primarily by the accelerated development of atherosclerotic disease. Moreover, reports show that diabetics have impaired lung functions. It has been proposed that insulin resistance leads to airway inflammation. Habib et al., *Nitric Oxide Measurement From Blood To Lungs, Is There A Link?* Pak J Physiol 2007; 3(1).

Nitric oxide is synthesized by the endothelium from L-arginine by nitric oxide synthase (NO synthase). NO synthase occurs in different isoforms, including a constitutive form (cNOS) and an inducible form (iNOS). The constitutive form is present in normal endothelial cells, neurons and some other tissues.

SUMMARY

The invention is directed on increase of efficiency of treatment of attention deficit hyperactivity disorder (ADHD) and attention deficit disorder (ADD).

In one aspect, the present invention provides pharmaceutical composition for treatment of attention deficit hyperactivity disorder, comprising activated-potentiated form of antibodies to brain-specific protein S-100 and activated-potentiated form of antibodies to endothelial NO synthase as an additional strengthening component.

In another aspect, the present invention provides pharmaceutical composition for treatment of attention deficit disorder, comprising activated-potentiated form of antibodies to brain-specific protein S-100 and activated-potentiated form of antibodies to endothelial NO synthase as an additional strengthening component.

In one variant, the present invention provides a combination pharmaceutical composition comprising activated-potentiated form of antibodies to brain-specific protein S-100 and activated-potentiated form of antibodies to endothelial NO synthase, wherein the antibody is to the entire protein S-100 or fragments thereof.

In one variant, the present invention provides a combination pharmaceutical composition comprising activated-potentiated form of antibodies to brain-specific protein S-100 and activated-potentiated form of antibodies to endothelial NO synthase, wherein the antibody is to the entire endothelial NO synthase or fragments thereof.

In one variant, the combination pharmaceutical composition of this aspect of the invention includes activated-potentiated form of an antibody to protein S-100 which is in the form of a mixture of (C12, C30, and C50) or (C12, C30 and C200) homeopathic dilutions impregnated onto a solid carrier. The activated-potentiated form of an antibody to endothelial NO synthase is in the form of mixture of (C12, C30, and C50) or (C12, C30 and C200) homeopathic dilutions may be subsequently impregnated onto the solid carrier.

In one variant, the combination pharmaceutical composition of this aspect of the invention includes activated-potentiated form of an antibody to NO synthase which is in the form of a mixture of (C12, C30, and C50) or (C12, C30 and C200) homeopathic dilutions impregnated onto a solid carrier. The activated-potentiated form of an antibody to protein S-100 is in the form of mixture of (C12, C30, and C50) or (C12, C30 and C200) homeopathic dilutions may be subsequently impregnated onto the solid carrier.

Preferably, the activated-potentiated form of an antibody to protein S-100 is a monoclonal, polyclonal or natural antibody, more preferably, a polyclonal antibody. In one variant of this aspect of the invention, the activated-potentiated form of an antibody to a protein S-100 is prepared by successive centesimal dilutions coupled with shaking of every dilution. Vertical shaking is specifically contemplated.

Preferably, the activated-potentiated form of an antibody to endothelial NO synthase is a monoclonal, polyclonal or natural antibody, more preferably, a polyclonal antibody. In one variant of this aspect of the invention, the activated-potentiated form of an antibody to endothelial NO synthase is prepared by successive centesimal dilutions coupled with shaking of every dilution. Vertical shaking is specifically contemplated.

In another aspect, the invention provides a method of treating attention deficit hyperactivity disorder, said method comprising administering to a patient in need thereof a combination pharmaceutical composition comprising a) an activated-potentiated form of an antibody to brain-specific protein S-100 and b) activated-potentiated form of antibodies to endothelial NO synthase.

In one variant of the invention, there is provided administration of from one to two unit dosage forms of the activated-potentiated form of an antibody to protein S-100 and one to two unit dosage forms of the activated-potentiated form of an antibody to NO synthase, each of the dosage form being administered from once daily to four times daily. Preferably, the one to two unit dosage forms of each of the activated-potentiated forms of antibodies is administered twice daily.

DESCRIPTION OF THE FIGURES

FIG. 1—Shows the reduction of evidence of ADHD symptoms (total score by the scale ADHDRS-IV-Home Version) over 2, 4, 6, 8, 12 weeks of therapy in comparison with baseline value.

DETAILED DESCRIPTION

The invention is defined with reference to the appended claims. With respect to the claims, the glossary that follows provides the relevant definitions.

The term "antibody" as used herein shall mean an immunoglobulin that specifically binds to, and is thereby defined as complementary with, a particular spatial and polar organization of another molecule. Antibodies as recited in the claims may include a complete immunoglobulin or fragment thereof, may be natural, polyclonal or monoclonal, and may include various classes and isotypes, such as IgA, IgD, IgE, IgG1, IgG2a, IgG2b and IgG3, IgM, etc. Fragments thereof may include Fab, Fv and F(ab')$_2$, Fab', and the like. The singular "antibody" includes plural "antibodies".

The term "activated-potentiated form" or "potentiated form" respectively, with respect to antibodies recited herein is used to denote a product of homeopathic potentization of any initial solution of antibodies. "Homeopathic potentization" denotes the use of methods of homeopathy to impart homeopathic potency to an initial solution of relevant substance. Although not so limited, 'homeopathic potentization" may involve, for example, repeated consecutive dilutions combined with external treatment, particularly vertical (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions (C12, C30, and C200) or the use of the mixture of three aqueous or aqueous-alcohol dilutions of the primary matrix solution of antibodies diluted $100^{12}$, $100^{30}$ and $100^{50}$ times, respectively, which is equivalent to centesimal homeopathic dilutions (C12, C30 and C50). Examples of homeopathic potentization are described in U.S. Pat. Nos. 7,572,441 and 7,582,294, which are incorporated herein by reference in their entirety and for the purpose stated. While the term "activated-potentiated form" is used in the claims, the term "ultra-low doses" is used in the examples. The term "ultra-low doses" became a term of art in the field of art created by study and use of homeopathically diluted and potentized form of substance. The term "ultra-low dose" or "ultra-low doses" is meant as fully supportive and primarily synonymous with the term 'activated-potentiated" form used in the claims.

In other words, an antibody is in the "activated-potentiated" or "potentiated" form when three factors are present. First, the "activated-potentiated" form of the antibody is a product of a preparation process well accepted in the homeopathic art. Second, the "activated-potentiated" form of antibody must have biological activity determined by methods well accepted in modern pharmacology. And third, the biological activity exhibited by the "activated potentiated" form of the antibody cannot be explained by the presence of the molecular form of the antibody in the final product of the homeopathic process.

For example, the activated potentiated form of antibodies may be prepared by subjecting an initial, isolated antibody in a molecular form to consecutive multiple dilutions coupled with an external impact, such as mechanical shaking. The external treatment in the course of concentration reduction may also be accomplished, for example, by exposure to ultrasonic, electromagnetic, or other physical factors. V. Schwabe "Homeopathic medicines", M., 1967, U.S. Pat. Nos. 7,229,648 and 4,311,897, which are incorporated by reference in their entirety and for the purpose stated, describe such processes that are well accepted methods of homeopathic potentiation in the homeopathic art. This procedure gives rise to a uniform decrease in molecular concentration of the initial molecular form of the antibody. This procedure is repeated until the desired homeopathic potency is obtained. For the individual antibody, the required homeopathic potency can be determined by subjecting the intermediate dilutions to biological testing in the desired pharmacological model. Although not so limited, 'homeopathic potentization" may involve, for example, repeated consecutive dilutions combined with external treatment, particularly (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably, water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions C12, C30 and C200 or the mixture of three aqueous or aqueous-alcohol dilutions of the primary matrix solution (mother tincture) of antibodies diluted $100^{12}$, $100^{30}$ and $100^{50}$ times, respectively, which is equivalent to centesimal homeopathic dilutions C12, C30 and C50. Examples of how to obtain the desired potency are also provided, for example, in U.S. Pat. Nos. 7,229,648 and 4,311,897, which are incorporated by reference for the purpose stated. The procedure applicable to the "activated potentiated" form of the antibodies described herein is described in more detail below.

There has been a considerable amount of controversy regarding homeopathic treatment of human subjects. While the present invention relies on accepted homeopathic processes to obtain the "activated-potentiated" form of antibodies, it does not rely solely on homeopathy in human subjects for evidence of activity. It has been surprisingly discovered by the inventor of the present application and amply demonstrated in the accepted pharmacological models that the solvent ultimately obtained from consecutive multiple dilution of a starting molecular form of an antibody has definitive activity unrelated to the presence of the traces of the molecular form of the antibody in the target dilution. The "activated-potentiated" form of the antibody provided herein are tested for biological activity in well accepted pharmacological models of activity, either in appropriate in vitro experiments, or in vivo in suitable animal models. The experiments provided further below provide evidence of biological activity in such models. Human clinical studies also provide evidence that the activity observed in the animal model is well translated to human therapy. Human studies have also provided evidence of availability of the "activated potentiated" forms described herein to treat specified human diseases or disorders well accepted as pathological conditions in the medical science.

Also, the claimed "activated-potentiated" form of antibody encompasses only solutions or solid preparations the biological activity of which cannot be explained by the presence of the molecular form of the antibody remaining from the initial, starting solution. In other words, while it is contemplated that the "activated-potentiated" form of the antibody may contain traces of the initial molecular form of the antibody, one skilled in the art could not attribute the observed biological activity in the accepted pharmacological models to the remaining molecular form of the antibody with any degree of plausibility due to the extremely low concentrations of the molecular form of the antibody remaining after the consecutive dilutions. While the invention is not limited by any specific theory, the biological activity of the "activated-potentiated' form of the antibodies of the present invention is not attributable to the initial molecular form of the antibody. Preferred is the "activated-potentiated" form of antibody in liquid or solid form in which the concentration of the initial molecular form of the antibody is below the limit of detection of the accepted analytical techniques, such as capillary electrophoresis and High Performance Liquid Chromatography.

Particularly preferred is the "activated-potentiated" form of antibody in liquid or solid form in which the concentration of the initial molecular form of the antibody is below the Avogadro number. In the pharmacology of molecular forms of therapeutic substances, it is common practice to create a dose-response curve in which the level of pharmacological response is plotted against the concentration of the active drug administered to the subject or tested in vitro. The minimal level of the drug which produces any detectable response is known as a threshold dose. It is specifically contemplated and preferred that the "activated-potentiated" form of the antibodies contains molecular antibody, if any, at a concentration below the threshold dose for the molecular form of the antibody in the given biological model.

The ADHD Rating Scale-IV refers to a tool both for diagnosing ADHD and for measuring improvements with treatment. (DuPaul G., et al. 1998). The scale contains 18 items that rates symptoms using a 4-point Likert-type severity scale (0=none, 1=mild, 2=moderate, and 3=severe). It is based on the DSM-IV (Diagnostic and statistic reference of mental disorders) criteria for ADHD. It has 9 items that assess inattentive symptoms and 9 items that assess hyperactive and impulsive symptoms. Sample rating questions include, "Avoids tasks (eg, schoolwork, homework) that require sustained mental effort" and "talks excessively." The ADHS Rating Scale has been developed and standardized as a rating scale for children. However, clinician-raters can be trained to successfully administer this scale to adults. According to the DSM-IV, ADHD can be divided into 3 subtypes: predominantly inattentive; predominantly hyperactive-impulsive; and the combined type, for which a patient must fully meet the criteria for both of the other 2 subtypes.

Inattentive symptoms include failure to pay close attention to detail, difficulty sustaining attention, not listening when spoken to, failure to follow through on instructions or finish tasks, difficulty organizing, reluctance to engage in activities that require sustained mental effort, often losing things, being easily distracted, and often being forgetful. A patient must have at least 6 of these 9 symptoms to be considered to have the inattentive subtype. The ADHD Rating Scale is available through Guilford Press.

The term "CGI-ADHD-Severity questionnaire" refers to the Clinical Global Impression rating scales that are commonly used to measure of symptom severity, treatment response and the efficacy of treatments in treatment studies of patients with mental disorders (Guy, W., 1976). The Clinical Global Impression Severity scale is a 7-point scale that requires the clinician to rate the severity of the patient's illness at the time of assessment, relative to the clinician's past experience with patients who have the same diagnosis. Considering total clinical experience, a patient is assessed on severity of mental illness at the time of rating 1=normal, not at all ill; 2, borderline mentally ill; 3, mildly ill; 4, moderately ill; 5, markedly ill; 6, severely ill; or 7, extremely ill.

In one aspect, the present invention provides a method of treating attention deficit hyperactivity disorder, the method comprising administering to a subject in need thereof a combination pharmaceutical composition consisting of a) an activated-potentiated form of an antibody to endothelial NO synthase and b) an activated-potentiated form of an antibody to brain-specific protein S-100. As set forth herein above, each of the individual components of the combination is generally known for its won individual medical uses. However, the inventors of the present application surprisingly discovered that administration of the combination is remarkably useful for the treatment of attention deficit hyperactivity disorder.

Preferably, for the purpose of treatment, the combination pharmaceutical composition is administered from once daily to four times daily, each administration including one or two combination unit dosage forms.

The pharmaceutical composition of the present application for the purpose of treatment of attention deficit hyperactivity disorder contains active components in volume primarily in 1:1 ratio.

For the purpose of treatment of attention deficit hyperactivity disorder the components of the pharmaceutical composition may be administered separately. However, the simultaneous administration of the combined components in one form of solutions and/or solid dosage form (tablet), which contains activated-potentiated form of antibodies to brain-specific protein S-100 and, accordingly, activated-potentiated form of antibodies to endothelial NO synthase is preferred.

In addition, during treatment of attention deficit hyperactivity disorder, separate and simultaneous application (intake to organism) of the declared pharmaceutical composition in the form of two separately prepared medications both in the form of solutions and solid dosage forms (tablets) each of which contains activated-potentiated form of antibodies to endothelial NO-synthase or to S-100 protein is possible.

The medical product is prepared mainly as follows.

The combination pharmaceutical composition in accordance with the present invention may be in the liquid form or in solid form. Each of the activated potentiated forms of the antibodies included in the pharmaceutical composition is prepared from an initial molecular form of the antibody via a process accepted in homeopathic art. The starting antibodies may be monoclonal, or polyclonal antibodies prepared in accordance with known processes, for example, as described in *Immunotechniques*, G. Frimel, M., "Meditsyna", 1987, p. 9-33; *"Hum. Antibodies. Monoclonal and recombinant antibodies, 30 years after"* by Laffly E., Sodoyer R.-2005-Vol. 14.-N 1-2. P. 33-55, both incorporated herein by reference.

Monoclonal antibodies may be obtained, e.g., by means of hybridoma technology. The initial stage of the process includes immunization based on the principles already developed in course of polyclonal antisera preparation. Further stages of work involve production of hybrid cells generating clones of antibodies with identical specificity. Their separate isolation is performed using the same methods as in case of polyclonal antisera preparation.

Polyclonal antibodies may be obtained via active immunization of animals. For this purpose, for example, suitable animals (e.g. rabbits) receive a series of injections of the appropriate antigen: brain-specific protein S-100 and endothelial NO synthase. The animals' immune system generates corresponding antibodies, which are collected from the animals in a known manner. This procedure enables preparation of a monospecific antibody-rich serum.

If desired, the serum containing antibodies may be purified, e.g., using affine chromatography, fractionation by salt precipitation, or ion-exchange chromatography. The resulting purified, antibody-enriched serum may be used as a starting material for preparation of the activated-potentiated form of the antibodies. The preferred concentration of the resulting initial solution of antibody in the solvent, preferably, water or water-ethyl alcohol mixture, ranges from about 0.5 to about 5.0 mg/ml.

The preferred procedure for preparing each component is the use of the mixture of three aqueous-alcohol dilutions of the primary matrix solution of antibodies diluted $100^{12}$, $100^{30}$ and $100^{200}$ times, respectively, which is equivalent to centesimal homeopathic dilutions C12, C30 and C200. To prepare a solid dosage form, a solid carrier is treated with the desired dilution obtained via the homeopathic process. To obtain a solid unit dosage form of the combination of the invention, the carrier mass is impregnated with each of the dilutions. Both orders of impregnation are suitable to prepare the desired combination dosage form.

In a preferred embodiment, the starting material for the preparation of the activated potentiated form that comprise the combination of the invention is polyclonal antibodies to brain-specific protein S-100 and endothelial NO synthase an initial (matrix) solution with concentration of 0.5 to 5.0 mg/ml is used for the subsequent preparation of activated-potentiated forms.

To prepare the pharmaceutical composition preferably polyclonal antibodies to brain-specific protein S-100 and endothelial NO synthase are used.

Polyclonal antibodies to endothelial NO synthase are obtained using adjuvant as immunogen (antigen) for immunization of rabbits and whole molecule of bovine endothelial NO synthase of the following sequence:

```
                                                       SEQ ID NO: 1
            Met Gly Asn Leu Lys Ser Val Gly Gln Glu Pro Gly Pro Pro Cys
            1               5                   10                  15

Gly Leu Gly Leu Gly Leu Gly Leu Gly Leu Cys Gly Lys Gln Gly
            16              20                  25                  30

Pro Ala Ser Pro Ala Pro Glu Pro Ser Arg Ala Pro Ala Pro Ala
            31              35                  40                  45

Thr Pro His Ala Pro Asp His Ser Pro Ala Pro Asn Ser Pro Thr
            46              50                  55                  60

Leu Thr Arg Pro Pro Glu Gly Pro Lys Phe Pro Arg Val Lys Asn
            61              65                  70                  75

Trp Glu Leu GLys er Ile Thr Tyr Asp Thr Leu Cys Ala Gln Ser
            76              80                  85                  90

Gln Gln Asp Gly Pro Cys Thr Pro Arg Cys Cys Leu GLys er Leu
            91              95                  100                 105

Val Leu Pro Arg Lys Leu Gln Thr Arg Pro Ser Pro Gly Pro Pro
            106             110                 115                 120
```

```
Pro Ala Glu Gln Leu Leu Ser Gln Ala Arg Asp Phe Ile Asn Gln
121             125             130             135

Tyr Tyr Ser Ser Ile Lys Arg Ser GLys er Gln Ala His Glu Glu
136             140             145             150

Arg Leu Gln Glu Val Glu Ala Glu Val Ala Ser Thr Gly Thr Tyr
151             155             160             165

His Leu Arg Glu Ser Glu Leu Val Phe Gly Ala Lys Gln Ala Trp
166             170             175             180

Arg Asn Ala Pro Arg Cys Val Gly Arg Ile Gln Trp Gly Lys Leu
181             185             190             195

Gln Val Phe Asp Ala Arg Asp Cys Ser Ser Ala Gln Glu Met Phe
196             200             205             210

Thr Tyr Ile Cys Asn His Ile Lys Tyr Ala Thr Asn Arg Gly Asn
211             215             220             225

Leu Arg Ser Ala Ile Thr Val Phe Pro Gln Arg Ala Pro Gly Arg
226             230             235             240

Gly Asp Phe Arg Ile Trp Asn Ser Gln Leu Val Arg Tyr Ala Gly
241             245             250             255

Tyr Arg Gln Gln Asp GLys er Val Arg Gly Asp Pro Ala Asn Val
256             260             265             270

Glu Ile Thr Glu Leu Cys Ile Gln His Gly Trp Thr Pro Gly Asn
271             275             280             285

Gly Arg Phe Asp Val Leu Pro Leu Leu Leu Gln Ala Pro Asp Glu
286             290             295             300

Ala Pro Glu Leu Phe Val Leu Pro Glu Leu Val Leu Glu Val
301             305             310             315

Pro Leu Glu His Pro Thr Leu Glu Trp Phe Ala Ala Leu Gly Leu
316             320             325             330

Arg Trp Tyr Ala Leu Pro Ala Val Ser Asn Met Leu Leu Glu Ile
331             335             340             345

Gly Gly Leu Glu Phe Ser Ala Ala Pro Phe Ser Gly Trp Tyr Met
346             350             355             360

Ser Thr Glu Ile Gly Thr Arg Asn Leu Cys Asp Pro His Arg Tyr
361             365             370             375

Asn Ile Leu Glu Asp Val Ala Val Cys Met Asp Leu Asp Thr Arg
376             380             385             390

Thr Thr Ser Ser Leu Trp Lys Asp Lys Ala Ala Val Glu Ile Asn
391             395             400             405

Leu Ala Val Leu His Ser Phe Gln Leu Ala Lys Val Thr Ile Val
406             410             415             420

Asp His His Ala Ala Thr Val Ser Phe Met Lys His Leu Asp Asn
421             425             430             435

Glu Gln Lys Ala Arg Gly Gly Cys Pro Ala Asp Trp Ala Trp Ile
436             440             445             450

Val Pro Pro Ile Ser GLys er Leu Thr Pro Val Phe His Gln Glu
451             455             460             465

Met Val Asn Tyr Ile Leu Ser Pro Ala Phe Arg Tyr Gln Pro Asp
466             470             475             480

Pro Trp Lys GLy Ser Ala Thr Lys Gly Ala Gly Ile Thr Arg Lys
481             485             490             495

Lys Thr Phe Lys Glu Val Ala Asn Ala Val Lys Ile Ser Ala Ser
496             500             505             510

Leu Met Gly Thr Leu Met Ala Lys Arg Val Lys Ala Thr Ile Leu
511             515             510             525
```

-continued

```
Tyr Ala Ser Glu Thr Gly Arg Ala Gln Ser Tyr Ala Gln Gln Leu
526                 530                 535                 540

Gly Arg Leu Phe Arg Lys Ala Phe Asp Pro Arg Val Leu Cys Met
541                 545                 550                 555

Asp Glu Tyr Asp Val Val Ser Leu Glu His Glu Ala Leu Val Leu
556                 560                 565                 570

Val Val Thr Ser Thr Phe Gly Asn Gly Asp Pro Pro Glu Asn Gly
571                 575                 580                 585

Glu Ser Phe Ala Ala Ala Leu Met Glu Met Ser Gly Pro Tyr Asn
586                 590                 595                 600

Ser Ser Pro Arg Pro Glu Gln His Lys Ser Tyr Lys Ile Arg Phe
601                 605                 610                 615

Asn Ser Val Ser Cys Ser Asp Pro Leu Val Ser Ser Trp Arg Arg
616                 620                 625                 630

Lys Arg Lys Glu Ser Ser Asn Thr Asp Ser Ala Gly Ala Leu Gly
631                 635                 640                 645

Thr Leu Arg Phe Cys Val Phe Gly Leu GLy Ser Arg Ala Tyr Pro
646                 650                 655                 660

His Phe Cys Ala Phe Ala Arg Ala Val Asp Thr Arg Leu Glu Glu
661                 665                 670                 675

Leu Gly Gly Glu Arg Leu Leu Gln Leu Gly Gln Gly Asp Glu Leu
676                 680                 685                 690

Cys Gly Gln Glu Glu Ala Phe Arg Gly Trp Ala Lys Ala Ala Phe
691                 695                 700                 705

Gln Ala Ser Cys Glu Thr Phe Cys Val Gly Glu Glu Ala Lys Ala
706                 710                 715                 720

Ala Ala Gln Asp Ile Phe Ser Pro Lys Arg Ser Trp Lys Arg Gln
721                 725                 730                 735

Arg Tyr Arg Leu Ser Thr Gln Ala Glu Gly Leu Gln Leu Leu Pro
736                 740                 745                 750

Gly Leu Ile His Val His Arg Arg Lys Met Phe Gln Ala Thr Val
751                 755                 760                 765

Leu Ser Val Glu Asn Leu Gln Ser Ser Lys Ser Thr Arg Ala Thr
766                 770                 775                 780

Ile Leu Val Arg Leu Asp Thr Ala Gly Gln Glu Gly Leu Gln Tyr
781                 785                 790                 795

Gln Pro Gly Asp His Ile Gly Ile Cys Pro Pro Asn Arg Pro Gly
796                 800                 805                 810

Leu Val Glu Ala Leu Leu Ser Arg Val Glu Asp Pro Pro Pro Pro
811                 815                 820                 825

Thr Glu Ser Val Ala Val Glu Gln Leu Glu Lys GLys er Pro Gly
826                 830                 835                 840

Gly Pro Pro Pro Ser Trp Val Arg Asp Pro Arg Leu Pro Pro Cys
841                 845                 850                 855

Thr Leu Arg Gln Ala Leu Thr Phe Phe Leu Asp Ile Thr Ser Pro
856                 860                 865                 870

Pro Ser Pro Arg Leu Leu Arg Leu Leu Ser Thr Leu Ala Glu Glu
871                 875                 880                 885

Pro Ser Glu Gln Gln Glu Leu Glu Thr Leu Ser Gln Asp Pro Arg
886                 890                 895                 900

Arg Tyr Glu Glu Trp Lys Trp Phe Arg Cys Pro Thr Leu Leu Glu
901                 905                 910                 915

Val Leu Glu Gln Phe Pro Ser Val Ala Leu Pro Ala Pro Leu Leu
916                 920                 925                 930
```

-continued

```
Leu Thr Gln Leu Pro Leu Leu Gln Pro Arg Tyr Tyr Ser Val Ser
931                 935                 940                 945

Ser Ala Pro Asn Ala His Pro Gly Glu Val His Leu Thr Val Ala
946                 950                 955                 960

Val Leu Ala Tyr Arg Thr Gln Asp Gly Leu Gly Pro Leu His Tyr
961                 965                 970                 975

Gly Val Cys Ser Thr Trp Leu Ser Gln Leu Lys Thr Gly Asp Pro
976                 980                 985                 990

Val Pro Cys Phe Ile Arg Gly Ala Pro Ser Phe Arg Leu Pro Pro
991                 995                 1000                1005

Asp Pro Tyr Val Pro Cys Ile Leu Val Gly Pro Gly Thr Gly Ile
1006                1010                1015                1020

Ala Pro Phe Arg Gly Phe Trp Gln Glu Arg Leu His Asp Ile Glu
1021                1025                1030                1035

Ser Lys Gly Leu Gln Pro Ala Pro Met Thr Leu Val Phe Gly Cys
1036                1140                1145                1050

Arg Cys Ser Gln Leu Asp His Leu Tyr Arg Asp Glu Val Gln Asp
1051                1155                1160                1065

Ala Gln Glu Arg Gly Val Phe Gly Arg Val Leu Thr Ala Phe Ser
1066                1170                1175                1080

Arg Glu Pro Asp Ser Pro Lys Thr Tyr Val Gln Asp Ile Leu Arg
1081                1185                1190                1095

Thr Glu Leu Ala Ala Glu Val His Arg Val Leu Cys Leu Glu Arg
1096                1100                1105                1110

Gly His Met Phe Val Cys Gly Asp Val Thr Met Ala Thr Ser Val
1111                1115                1120                1125

Leu Gln Thr Val Gln Arg Ile Leu Ala Thr Glu Gly Asp Met Glu
1126                1130                1135                1140

Leu Asp Glu Ala Gly Asp Val Ile Gly Val Leu Arg Asp Gln Gln
1141                1145                1150                1155

Arg Tyr His Glu Asp Ile Phe Gly Leu Thr Leu Arg Thr Gln Glu
1156                1160                1165                1170

Val Thr Ser Arg Ile Arg Thr Gln Ser Phe Ser Leu Gln Glu Arg
1171                1175                1180                1185

His Leu Arg Gly Ala Val Pro Trp Ala Phe Asp Pro Pro Gly Pro
1186                1190                1195                1200

Asp Thr Pro Gly Pro
1201            1205
```

Polyclonal antibodies to endothelial NO synthase may be obtained using the whole molecule of human endothelial NO synthase of the following sequence:

```
                                               SEQ ID NO: 2
Met Gly Asn Leu Lys Ser Val Ala Gln Glu Pro Gly Pro Pro Cys
1               5                   10                  15

Gly Leu Gly Leu Gly Leu Gly Leu Gly Leu Cys Gly Lys Gln Gly
16              20                  25                  30

Pro Ala Thr Pro Ala Pro Glu Pro Ser Arg Ala Pro Ala Ser Leu
31              35                  40                  45

Leu Pro Pro Ala Pro Glu His Ser Pro Pro Ser Ser Pro Leu Thr
46              50                  55                  60

Gln Pro Pro Glu Gly Pro Lys Phe Pro Arg Val Lys Asn Trp Glu
61              65                  70                  75
```

-continued

```
Val GLys er Ile Thr Tyr Asp Thr Leu Ser Ala Gln Ala Gln Gln
 76              80                  85                  90

Asp Gly Pro Cys Thr Pro Arg Arg Cys Leu GLys er Leu Val Phe
 91              95                 100                 105

Pro Arg Lys Leu Gln Gly Arg Pro Ser Pro Gly Pro Pro Ala Pro
106             110                 115                 120

Glu Gln Leu Leu Ser Gln Ala Arg Asp Phe Ile Asn Gln Tyr Tyr
121             125                 130                 135

Ser Ser Ile Lys Arg Ser GLys er Gln Ala His Glu Gln Arg Leu
136             140                 145                 150

Gln Glu Val Glu Ala Glu Val Ala Ala Thr Gly Thr Tyr Gln Leu
151             155                 160                 165

Arg Glu Ser Glu Leu Val Phe Gly Ala Lys Gln Ala Trp Arg Asn
166             170                 175                 180

Ala Pro Arg Cys Val Gly Arg Ile Gln Trp Gly Lys Leu Gln Val
181             185                 190                 195

Phe Asp Ala Arg Asp Cys Arg Ser Ala Gln Glu Met Phe Thr Tyr
196             200                 205                 210

Ile Cys Asn His Ile Lys Tyr Ala Thr Asn Arg Gly Asn Leu Arg
211             215                 220                 225

Ser Ala Ile Thr Val Phe Pro Gln Arg Cys Pro Gly Arg Gly Asp
226             230                 235                 240

Phe Arg Ile Trp Asn Ser Gln Leu Val Arg Tyr Ala Gly Tyr Arg
241             245                 250                 255

Gln Gln Asp GLy Ser Val Arg Gly Asp Pro Ala Asn Val Glu Ile
256             260                 265                 270

Thr Glu Leu Cys Ile Gln His Gly Trp Thr Pro Gly Asn Gly Arg
271             275                 280                 285

Phe Asp Val Leu Pro Leu Leu Leu Gln Ala Pro Asp Glu Pro Pro
286             290                 295                 300

Glu Leu Phe Leu Leu Pro Pro Glu Leu Val Leu Glu Val Pro Leu
301             305                 310                 315

Glu His Pro Thr Leu Glu Trp Phe Ala Ala Leu Gly Leu Arg Trp
316             320                 325                 330

Tyr Ala Leu Pro Ala Val Ser Asn Met Leu Leu Glu Ile Gly Gly
331             335                 340                 345

Leu Glu Phe Pro Ala Ala Pro Phe Ser Gly Trp Tyr Met Ser Thr
346             350                 355                 360

Glu Ile Gly Thr Arg Asn Leu Cys Asp Pro His Arg Tyr Asn Ile
361             365                 370                 375

Leu Glu Asp Val Ala Val Cys Met Asp Leu Asp Thr Arg Thr Thr
376             380                 385                 390

Ser Ser Leu Trp Lys Asp Lys Ala Ala Val Glu Ile Asn Val Ala
391             395                 400                 405

Val Leu His Ser Tyr Gln Leu Ala Lys Val Thr Ile Val Asp His
406             410                 415                 420

His Ala Ala Thr Ala Ser Phe Met Lys His Leu Glu Asn Glu Gln
421             425                 430                 435

Lys Ala Arg Gly Gly Cys Pro Ala Asp Trp Ala Trp Ile Val Pro
436             440                 445                 450

Pro Ile Ser GLys er Leu Thr Pro Val Phe His Gln Glu Met Val
451             455                 460                 465

Asn Tyr Phe Leu Ser Pro Ala Phe Arg Tyr Gln Pro Asp Pro Trp
466             470                 475                 480
```

-continued

```
Lys Gly Ser Ala Ala Lys Gly Thr Gly Ile Thr Arg Lys Lys Thr
481             485                 490                 495

Phe Lys Glu Val Ala Asn Ala Val Lys Ile Ser Ala Ser Leu Met
496             500                 505                 510

Gly Thr Val Met Ala Lys Arg Val Lys Ala Thr Ile Leu Tyr Gly
511             515                 510                 525

Ser Glu Thr Gly Arg Ala Gln Ser Tyr Ala Gln Gln Leu Gly Arg
526             530                 535                 540

Leu Phe Arg Lys Ala Phe Asp Pro Arg Val Leu Cys Met Asp Glu
541             545                 550                 555

Tyr Asp Val Val Ser Leu Glu His Glu Thr Leu Val Leu Val Val
556             560                 565                 570

Thr Ser Thr Phe Gly Asn Gly Asp Pro Pro Glu Asn Gly Glu Ser
571             575                 580                 585

Phe Ala Ala Ala Leu Met Glu Met Ser Gly Pro Tyr Asn Ser Ser
586             590                 595                 600

Pro Arg Pro Glu Gln His Lys Ser Tyr Lys Ile Arg Phe Asn Ser
601             605                 610                 615

Ile Ser Cys Ser Asp Pro Leu Val Ser Ser Trp Arg Arg Lys Arg
616             620                 625                 630

Lys Glu Ser Ser Asn Thr Asp Ser Ala Gly Ala Leu Gly Thr Leu
631             635                 640                 645

Arg Phe Cys Val Phe Gly Leu GLys er Arg Ala Tyr Pro His Phe
646             650                 655                 660

Cys Ala Phe Ala Arg Ala Val Asp Thr Arg Leu Glu Glu Leu Gly
661             665                 670                 675

Gly Glu Arg Leu Leu Gln Leu Gly Gln Gly Asp Glu Leu Cys Gly
676             680                 685                 690

Gln Glu Glu Ala Phe Arg Gly Trp Ala Gln Ala Ala Phe Gln Ala
691             695                 700                 705

Ala Cys Glu Thr Phe Cys Val Gly Glu Asp Ala Lys Ala Ala Ala
706             710                 715                 720

Arg Asp Ile Phe Ser Pro Lys Arg Ser Trp Lys Arg Gln Arg Tyr
721             725                 730                 735

Arg Leu Ser Ala Gln Ala Glu Gly Leu Gln Leu Leu Pro Gly Leu
736             740                 745                 750

Ile His Val His Arg Arg Lys Met Phe Gln Ala Thr Ile Arg Ser
751             755                 760                 765

Val Glu Asn Leu Gln Ser Ser Lys Ser Thr Arg Ala Thr Ile Leu
766             770                 775                 780

Val Arg Leu Asp Thr Gly Gly Gln Glu Gly Leu Gln Tyr Gln Pro
781             785                 790                 795

Gly Asp His Ile Gly Val Cys Pro Pro Asn Arg Pro Gly Leu Val
796             800                 805                 810

Glu Ala Leu Leu Ser Arg Val Glu Asp Pro Pro Ala Pro Thr Glu
811             815                 820                 825

Pro Val Ala Val Glu Gln Leu Glu Lys Gly Ser Pro Gly Gly Pro
826             830                 835                 840

Pro Pro Gly Trp Val Arg Asp Pro Arg Leu Pro Pro Cys Thr Leu
841             845                 850                 855

Arg Gln Ala Leu Thr Phe Phe Leu Asp Ile Thr Ser Pro Pro Ser
856             860                 865                 870

Pro Gln Leu Leu Arg Leu Leu Ser Thr Leu Ala Glu Glu Pro Arg
871             875                 880                 885
```

-continued

```
Glu Gln Gln Glu Leu Ala Leu Ser Gln Asp Pro Arg Arg Tyr
886                 890                 895                 900

Glu Glu Trp Lys Trp Phe Arg Cys Pro Thr Leu Leu Glu Val Leu
901                 905                 910                 915

Glu Gln Phe Pro Ser Val Ala Leu Pro Ala Pro Leu Leu Leu Thr
916                 920                 925                 930

Gln Leu Pro Leu Leu Gln Pro Arg Tyr Tyr Ser Val Ser Ser Ala
931                 935                 940                 945

Pro Ser Thr His Pro Gly Glu Ile His Leu Thr Val Ala Val Leu
946                 950                 955                 960

Ala Tyr Arg Thr Gln Asp Gly Leu Gly Pro Leu His Tyr Gly Val
961                 965                 970                 975

Cys Ser Thr Trp Leu Ser Gln Leu Lys Pro Gly Asp Pro Val Pro
976                 980                 985                 990

Cys Phe Ile Arg Gly Ala Pro Ser Phe Arg Leu Pro Pro Asp Pro
991                 995                 1000                1005

Ser Leu Pro Cys Ile Leu Val Gly Pro Gly Thr Gly Ile Ala Pro
1006                1010                1015                1020

Phe Arg Gly Phe Trp Gln Glu Arg Leu His Asp Ile Glu Ser Lys
1021                1025                1030                1035

Gly Leu Gln Pro Thr Pro Met Thr Leu Val Phe Gly Cys Arg Cys
1036                1140                1145                1050

Ser Gln Leu Asp His Leu Tyr Arg Asp Glu Val Gln Asn Ala Gln
1051                1155                1160                1065

Gln Arg Gly Val Phe Gly Arg Val Leu Thr Ala Phe Ser Arg Glu
1066                1170                1175                1080

Pro Asp Asn Pro Lys Thr Tyr Val Gln Asp Ile Leu Arg Thr Glu
1081                1085                1090                1095

Leu Ala Ala Glu Val His Arg Val Leu Cys Leu Glu Arg Gly His
1096                1100                1105                1110

Met Phe Val Cys Gly Asp Val Thr Met Ala Thr Asn Val Leu Gln
1111                1115                1120                1125

Thr Val Gln Arg Ile Leu Ala Thr Glu Gly Asp Met Glu Leu Asp
1126                1130                1135                1140

Glu Ala Gly Asp Val Ile Gly Val Leu Arg Asp Gln Gln Arg Tyr
1141                1145                1150                1155

His Glu Asp Ile Phe Gly Leu Thr Leu Arg Thr Gln Glu Val Thr
1156                1160                1165                1170

Ser Arg Ile Arg Thr Gln Ser Phe Ser Leu Gln Glu Arg Gln Leu
1171                1175                1180                1185

Arg Gly Ala Val Pro Trp Ala Phe Asp Pro Pro Gly Ser Asp Thr
1186                1190                1195                1200

Asn Ser Pro
1201    1203
```

To obtain polyclonal antibodies to endothelial NO synthase, it is also possible to use a fragment of endothelial NO synthase, selected, for example, from the following sequences:

SEQ ID NO: 3
```
Pro Trp Ala Phe
1192        1195
```

SEQ ID NO: 4
```
Gly Ala Val Pro
1189        1192
```

-continued

SEQ ID NO: 5
Arg
1185

His Leu Arg Gly Ala Val Pro Trp Ala Phe Asp Pro Pro Gly Pro
1186            1190            1195            1200

Asp Thr Pro Gly Pro
1201        1205

SEQ ID NO: 6
Ala Phe Asp Pro Pro Gly Pro
11941195                1200

Asp Thr Pro Gly Pro
1201        1205

SEQ ID NO: 7
His Leu Arg Gly Ala Val Pro Trp Ala Phe Asp
1186            1190            11951196

SEQ ID NO: 8
His Leu Arg Gly Ala Val Pro Trp Ala Phe Asp Pro Pro Gly Pro
1186            1190            1195            1200

Asp Thr Pro Gly Pro
1201        1205

The exemplary procedure for preparation of starting polyclonal antibodies to endothelial NO synthase may be described as follows: 7-9 days before blood sampling 1-3 intravenous injections are made to the rabbits to increase the level of polyclonal antibodies in the rabbit blood stream. Upon immunization, blood samples are taken to test the antibody level. Typically, the maximum level of the immune reaction of the soluble antigen is reached in 40-60 days after the first injection. After the termination of the first immunization cycle, rabbits have a 30-day rehabilitation period, after which re-immunization is performed with another 1-3 intravenous injections.

To obtain antiserum containing the desired antibodies, the immunized rabbits' blood is collected from rabbits and placed in a 50 ml centrifuge tube Product clots formed on the tube sides are removed with a wooden spatula, and a rod is placed into the clot in the tube center. The blood is then placed in a refrigerator for one night at the temperature of about 4° C. On the following day, the clot on the spatula is removed, and the remaining liquid is centrifuged for 10 min at 13,000 rotations per minute. Supernatant fluid is the target antiserum. The obtained antiserum is typically yellow. 20% of $NaN_3$ (weight concentration) is added in the antiserum to a final concentration of 0.02% and stored before use in frozen state at the temperature of −20° C. (or without addition $NaN_3$—at temperature −70° C.). To separate the target antibodies to endothelial NO synthase from the antiserum, the following solid phase absorption sequence is suitable:

(a) 10 ml of antiserum of rabbit is diluted twofold with 0.15 M NaCl, after which 6.26 g $Na_2SO_4$, is added, mixed and incubated for about 12-16 hours at 4° C.;

(b) the sediment is removed by centrifugation, dissolved in 10 ml of phosphate buffer and dialyzed against the same buffer within one night at room temperature;

(c) after the sediment is removed by centrifugation, the solution is put on the column with DEAE-cellulose, counterbalanced by phosphate buffer;

(d) the antibody fraction is determined by measuring the optical density of eluate at 280 nanometers.

The isolated crude antibodies are purified using affine chromatography method by attaching the obtained antibodies to endothelial NO synthase located on the insoluble matrix of the chromatography media, with subsequent elution by concentrated aqueous salt solutions.

The resulting buffer solution is used as the initial solution for the homeopathic dilution process used to prepare the activated potentiated form of the antibodies. The preferred concentration of the initial matrix solution of the antigen-purified polyclonal rabbit antibodies to endothelial NO synthase is 0.5 to 5.0 mg/ml, preferably, 2.0 to 3.0 mg/ml.

The brain-specific S100 protein, expressed by neurons and glial cells (astrocytes and oligodendrocytes), directly or through interactions with other proteins executes in the CNS a number of functions directed at maintaining normal brain functioning, including affecting learning and memory processes, growth and viability of neurons, regulation of metabolic processes in neuronal tissues and others. To obtain polyclonal antibodies to brain-specific protein S-100, brain-specific protein S-100 is used, which physical and chemical properties are described in the article of M. V. Starostin, S. M. Sviridov, Neurospecific Protein S-100, *Progress of Modern Biology*, 1977, Vol. 5, P. 170-178; found in the book M. B. Shtark, *Brain-Specific Protein Antigenes and Functions of Neuron*, "Medicine", 1985; P. 12-14. Brain-specific protein S-100 is allocated from brain tissue of the bull by the following technique:

the bull brain tissue frozen in liquid nitrogen is converted into powder using a specialized mill;
proteins are extracted in the ratio of 1:3 (weight/volume) using an extracting buffer with homogenization;
the homogenate is heated for 10 min at 60° C. and then cooled to 4° C. in an ice bath;
thermolabile proteins are removed by centrifugation;
ammonium sulfate fractionation is carried out in stages, with subsequent removal of precipitated proteins;
the fraction containing S-100 protein is precipitated using 100% saturated ammonium sulfate accomplished by pH drop to 4.0; the desired fraction is collected by centrifugation;
the precipitate is dissolved in a minimum buffer volume containing EDTA and mercaptoethanol, the precipitate is dialyzed with deionized water and lyophilized;
fractionation of acidic proteins is followed by chromatography in ion-exchanging media, DEAE-cellulose DE-52 and then DEAE-sephadex A-50;

the collected and dialyzed fractions, which contain S-100 protein, are divided according to molecular weight by gel filtration on sephadex G-100;

purified S-100 protein is dialyzed and lyophilized.

The molecular weight of the purified brain-specific protein S-100 is 21000 D.

Owing to the high concentration of asparaginic and glutaminic acids brain-specific protein S-100 is highly acidic and occupies extreme anode position during electroendosmosis in a discontinuous buffer system of polyacrylamide gel which facilitates its identification.

The polyclonal antibodies to S-100 protein may also be obtained by a similar methodology to the methodology described for endothelial NO synthase antibodies using an adjuvant. The entire molecule of S-100 protein may be used as immunogen (antigen) for rabbits' immunization:

```
Bovine S100B
                                                    (SEQ ID NO: 9)
Met Ser Glu Leu Glu Lys Ala Val Val Ala Leu Ile Asp Val Phe
1               5                   10                  15

His Gln Tyr Ser Gly Arg Glu Gly Asp Lys His Lys Leu Lys Lys
16              20                  25                  30

Ser Glu Leu Lys Glu Leu Ile Asn Asn Glu Leu Ser His Phe Leu
31              35                  40                  45

Glu Glu Ile Lys Glu Gln Glu Val Val Asp Lys Val Met Glu Thr
46              50                  55                  60

Leu Asp Ser Asp Gly Asp Gly Glu Cys Asp Phe Gln Glu Phe Met
61              65                  70                  75

Ala Phe Val Ala Met Ile Thr Thr Ala Cys His Glu Phe Phe Glu
76              80                  85                  90

His Glu
91  92

Human S100B
                                                    (SEQ ID NO: 10)
Met Ser Glu Leu Glu Lys Ala Met Val Ala Leu Ile Asp Val Phe
1               5                   10                  15

His Gln Tyr Ser Gly Arg Glu Gly Asp Lys His Lys Leu Lys Lys
16              20                  25                  30

Ser Glu Leu Lys Glu Leu Ile Asn Asn Glu Leu Ser His Phe Leu
31              35                  40                  45

Glu Glu Ile Lys Glu Gln Glu Val Val Asp Lys Val Met Glu Thr
46              50                  55                  60

Leu Asp Asn Asp Gly Asp Gly Glu Cys Asp Phe Gln Glu Phe Met
61              65                  70                  75

Ala Phe Val Ala Met Val Thr Thr Ala Cys His Glu Phe Phe Glu
76              80                  85                  90

His Glu
91  92

Human S100A1
                                                    (SEQ ID NO: 11)
Met Gly Ser Glu Leu Glu Thr Ala Met Glu Thr Leu Ile Asn Val
1               5                   10                  15

Phe His Ala His Ser Gly Lys Glu Gly Asp Lys Tyr Lys Leu Ser
16              20                  25                  30

Lys Lys Glu Leu Lys Glu Leu Leu Gln Thr Glu Leu Ser Gly Phe
31              35                  40                  45

Leu Asp Ala Gln Lys Asp Val Asp Ala Val Asp Lys Val Met Lys
46              50                  55                  60

Glu Leu Asp Glu Asn Gly Asp Gly Glu Val Asp Phe Gln Glu Tyr
61              65                  70                  75

Val Val Leu Val Ala Ala Leu Thr Val Ala Cys Asn Asn Phe Phe
76              80                  85                  90

Trp Glu Asn Ser
91          94
```

-continued

Bovine S100A1
(SEQ ID NO: 12)

```
Met Gly Ser Glu Leu Glu Thr Ala Met Glu Thr Leu Ile Asn Val
 1           5                  10                      15

Phe His Ala His Ser Gly Lys Glu Gly Asp Lys Tyr Lys Leu Ser
16              20                  25                  30

Lys Lys Glu Leu Lys Glu Leu Leu Gln Thr Glu Leu Ser Gly Phe
31              35                  40                  45

Leu Asp Ala Gln Lys Asp Ala Asp Ala Val Asp Lys Val Met Lys
46              50                  55                  60

Glu Leu Asp Glu Asn Gly Asp Gly Glu Val Asp Phe Gln Glu Tyr
61              65                  70                  75

Val Val Leu Val Ala Ala Leu Thr Val Ala Cys Asn Asn Phe Phe
76              80                  85                  90

Trp Glu Asn Ser
91              94
```

To obtain antiserum, brain-specific S-100 protein or the mixture of S-100 protein s (antigens) in complex with methylated bull seralbumin as the carrying agent with full Freund's adjuvant is prepared and added to allocated brain-specific protein S-100 which is injected subdermally to a laboratory animal—a rabbit into area of back in quantity of 1-2 ml. On 8th, 15th day repeated immunization is made. Blood sampling is made (for example, from a vein in the ear) on the 26th and the 28th day.

The obtained antiserum titre is 1:500-1:1000, forms single precipitin band with an extract of nervous tissue but does not react with extracts of heterological bodies and forms single precipitin peak both with pure protein S-100 and with the extract of nervous tissue indicating that the antiserum obtained is monospecific.

The activated potentiated form of each component of the combination may be prepared from an initial solution by homeopathic potentization, preferably using the method of proportional concentration decrease by serial dilution of 1 part of each preceding solution (beginning with the initial solution) in 9 parts (for decimal dilution), or in 99 parts (for centesimal dilution), or in 999 parts (for millesimal dilution—attenuation M) of a neutral solvent, starting with a concentration of the initial solution of antibody in the solvent, preferably, water or a water-ethyl alcohol mixture, in the range from about 0.5 to about 5.0 mg/ml, coupled with external impact. Preferably, the external impact involves multiple vertical shaking (dynamization) of each dilution. Preferably, separate containers are used for each subsequent dilution up to the required potency level, or the dilution factor. This method is well-accepted in the homeopathic art. See, e.g. V. Schwabe "Homeopathic medicines", M., 1967, p. 14-29, incorporated herein by reference for the purpose stated.

For example, to prepare a 12-centesimal dilution (denoted C12), one part of the initial matrix solution of antibodies to brain-specific protein S-100 (or to endothelial NO—synthase) with the concentration of 2.5 mg/ml is diluted in 99 parts of neutral aqueous or aqueous-alcohol solvent (preferably, 15%-ethyl alcohol) and then vertically shaken many times (10 and more) to create the 1st centesimal dilution (denoted as C1). The 2nd centesimal dilution (C2) is prepared from the 1st centesimal dilution C1. This procedure is repeated 11 times to prepare the 12th centesimal dilution C12. Thus, the 12th centesimal dilution C12 represents a solution obtained by 12 serial dilutions of one part of the initial matrix solution of antibodies to brain-specific protein S-100 with the concentration of 2.5 mg/ml in 99 parts of a neutral solvent in different containers, which is equivalent to the centesimal homeopathic dilution C12. Similar procedures with the relevant dilution factor are performed to obtain dilutions C30, C50 and C200. The intermediate dilutions may be tested in a desired biological model to check activity. The preferred activated potentiated forms for both antibodies comprising the combination of the invention are a mixture of C12, C30, and C200 dilutions or C12, C30 and C50 dilutions. When using the mixture of various homeopathic dilutions (primarily centesimal) of the active substance as biologically active liquid component, each component of the composition (e.g., C12, C30, C50, C200) is prepared separately according to the above-described procedure until the next-to-last dilution is obtained (e.g., until C11, C29, C49 and C199 respectively), and then one part of each component is added in one container according to the mixture composition and mixed with the required quantity of the solvent (e.g. with 97 parts for centesimal dilution).

Thus, activated-potentiated form of antibodies to brain-specific protein S-100 in ultra low dose is obtained by extra attenuation of matrix solution, accordingly in $100^{12}$, $100^{30}$ and $100^{200}$ times, equal to centesimal C12, C30 and C200 solutions or $100^{12}$, $100^{30}$ and $100^{50}$ times, equal to centesimal C12, C30 and C50 solutions prepared on homoeopathic technology.

Use of active substance in the form of mixture of other various solutions on homoeopathic technology, for example, decimal and/or centesimal, (C12, C30, C100; C12, C30, C50; D20, C30, C100 or D10, C30, M100 etc.) is possible. The efficiency is defined experimentally.

External processing in the course of potentiation and concentration reduction can also be carried out by means of ultrasound, of electromagnetic or any other physical influence accepted in the homeopathic art.

Preferably, the combination pharmaceutical composition of the invention may be in the form of a liquid or in the solid unit dosage form. The preferred liquid form of the pharmaceutical composition is a mixture, preferably, at a 1:1 ratio of the activated potentiated form of antibodies to endothelial NO synthase and the activated potentiated form of antibodies to protein S-100. The preferred liquid carrier is water or water-ethyl alcohol mixture.

The solid unit dosage form of the pharmaceutical composition of the invention may be prepared by using impregnating a solid, pharmaceutically acceptable carrier with the mixture of the activated potentiated form aqueous or aqueous-alcohol solutions of active components that are mixed, primarily in 1:1 ratio and used in liquid dosage form. Alternatively, the carrier may be impregnated consecutively with each requisite dilution. Both orders of impregnation are acceptable.

Preferably, the pharmaceutical composition in the solid unit dosage form is prepared from granules of the pharmaceutically acceptable carrier which was previously saturated with the aqueous or aqueous-alcoholic dilutions of the activated potentiated form of antibodies. The solid dosage form may be in any form known in the pharmaceutical art, including a tablet, a capsule, a lozenge, and others. As an inactive pharmaceutical ingredients one can use glucose, sucrose, maltose, amylum, isomaltose, isomalt and other mono- oligo- and polysaccharides used in manufacturing of pharmaceuticals as well as technological mixtures of the above mentioned inactive pharmaceutical ingredients with other pharmaceutically acceptable excipients, for example isomalt, crospovidone, sodium cyclamate, sodium saccharine, anhydrous citric acid etc), including lubricants, disintegrants, binders and coloring agents. The preferred carriers are lactose and isomalt. The pharmaceutical dosage form may further include standard pharmaceutical excipients, for example, microcrystalline cellulose, magnesium stearate and citric acid.

The example of preparation of the solid unit dosage form is set forth below. To prepare the solid oral form, 100-300 μm granules of lactose are impregnated with aqueous or aqueous-alcoholic solutions of the activated-potentiated form of antibodies to endothelial NO synthase and the activated potentiated form of antibodies to protein S-100 in the ratio of 1 kg of antibody solution to 5 or 10 kg of lactose (1:5 to 1:10). To effect impregnation, the lactose granules are exposed to saturation irrigation in the fluidized boiling bed in a boiling bed plant (e.g. "Huttlin Pilotlab" by Huttlin GmbH) with subsequent drying via heated air flow at a temperature below 40° C. The estimated quantity of the dried granules (10 to 34 weight parts) saturated with the activated potentiated form of antibodies is placed in the mixer, and mixed with 25 to 45 weight parts of "non-saturated" pure lactose (used for the purposes of cost reduction and simplification and acceleration of the technological process without decreasing the treatment efficiency), together with 0.1 to 1 weight parts of magnesium stearate, and 3 to 10 weight parts of microcrystalline cellulose. The obtained tablet mass is uniformly mixed, and tableted by direct dry pressing (e.g., in a Korsch—XL 400 tablet press) to form 150 to 500 mg round pills, preferably, 300 mg. After tableting, 300 mg pills are obtained that are saturated with aqueous-alcohol solution (3.0-6.0 mg/pill) of the combination of the activated-potentiated form of antibodies. Each component of the combination used to impregnate the carrier is in the form of a mixture of centesimal homeopathic dilutions, preferably, C12, C30 and C200.

Preferably, 1-2 tablets of the claimed pharmaceutical composition are administered 2-4 times a day.

The claimed pharmaceutical composition as well as its components does not possess sedative and myorelaxant effect, does not cause addiction and habituation.

EXAMPLES

Example 1

Study of the effect of a complex preparation containing ultralow doses of activated—potentiated forms of polyclonal affinity purified rabbit antibodies to brain-specific protein S-100 (anti-S100) and endothelial NO-synthase (anti-eNOS), obtained by super-dilution of initial matrix solution (concentration: 2.5 mg/ml) ($100^{12}$, $100^{30}$, $100^{200}$ times), equivalent to a mixture of centesimal homeopathic dilutions C12, C30, C200 (ratio: 1:1) ("ULD of anti-S100+anti-eNOS"), as well as its components: ultra-low doses of affinity purified rabbit antibodies to brain-specific protein S-100, purified on antigen, obtained by super-dilution of initial matrix solution ($100^{12}$, $100^{30}$, $100^{200}$ times, equivalent to a mixture of centesimal homeopathic dilution C12, C30, C200 ("ULD of anti-S100"), and ultra-low doses of polyclonal affinity purified rabbit antibodies to endothelial NO-synthase, obtained by super-dilution of initial matrix solution ($100^{12}$, $100^{30}$, $100^{200}$ times), equivalent to a mixture of centesimal homeopathic dilution C12, C30, C200 ("ULD of anti-eNOS") on in vitro on binding of standard ligand [$^3$H]pentazocine to human recombinant σ1 receptor was evaluated using radioligand method. Potentiated distilled water (mixture of homeopathic dilutions C12+C30+C200) was used as test preparations control.

The sigma-1 (σ1) receptor is an intracellular receptor which is localized in the cells of central nervous system, the cells of the most of peripheral tissues and immune component cells. These receptors exhibit a unique ability to be translocated which is thought to be caused by many psychotropic medications. The dynamics of sigma-1 receptors is directly linked to various influences which are performed by preparations acting to the sigma-1 receptors. These effects include, the regulation of activity channels, ecocytosis, signal transferring, remodeling of the plasma membrane (formation of rafts) and lipid transportation/metabolism, all of which can contribute to the plasticity of neurons in a brain. There is evidence that the sigma-1 receptors have a modulating effect on all the major neuromediator systems: noradrenergic, serotonergic, dopaminergic, cholinergic systems and NMDA-adjustable glutamate effects. Sigma-1 receptors play an important role in the pathophysiology of neurodegenerative diseases (e.g., Alzheimer's disease, Parkinson's disease), psychiatric and affective disorders and stroke; and they also take part in the processes of learning and memory. In this regard, the ability of drugs to influence the efficiency of interaction of ligands with sigma-1 receptor is indicative of the presence of neuroprotective, anti-ischemic, anxiolytic, antidepressant and anti astenic components in the spectrum of its pharmacological activity and permits the consideration of these drugs as effective preparations particularly for the treatment of cerebrovascular diseases.

During the test (to measure total binding) 20 μl of the complex preparation of ULD of anti-S100+anti-eNOS or 10 μl of ULD of anti-S100 or 10 μl of ULD of anti-NOS were added to the incubation medium. Thus, the quantity of ULD of anti-S100+anti-eNOS transferred into the test basin when testing the complex preparation was identical to that of ULD of anti-S100 and ULD of anti-NOS tested as monopreparations, which allows for a comparison of the efficiency of the preparation to its separate components. 20 μl and 10 μl of potentiated water were transferred into the incubation medium.

Further, 160 μl (about 200 μg of protein) of Jurkat cell line membranes homogenate (human leukemic T-lymphocyte line), and finally, 20 μl of tritium-labeled radioligand [$^3$H] pentazocine (15 nm) were transferred.

In order to measure non-specific binding, 20 μl of non-labeled ligand-haloperidol (10 μM) were transferred in the incubation medium instead of the preparations or potentiated water.

Radioactivity was measured using a scintillometer (Topcount, Packard) and scintillation blend (Microscint 0, Packard) following the incubation within 120 minutes at 22° C. in 50 mM Tris-HCl buffer (pH=7.4) and filtration using fiberglass filters (GF/B, Packard). Specific binding (during the test or control) was calculated as a difference between total (during the test or control) and non-specific binding.

Results are represented as percentage of specific binding inhibition in control (distilled water was used as control) (Table 1).

TABLE 1

| Test group | Quantity per test basin | % of radioligand specific binding in control | | | % of radioligand binding inhibition in control |
|---|---|---|---|---|---|
| | | 1$^{st}$ test | 2$^{nd}$ test | Average | |
| ULD of anti-S100 + anti-eNOS | 20 μl | 48.4 | 35.5 | 42.0 | 58.0 |
| ULD of anti-S100 | 10 μl | 67.3 | 63.1 | 65.2 | 34.8 |
| ULD of anti-eNOS | 10 μl | 147.5 | 161.1 | 154.3 | −54.3 |
| Potentiated water | 20 μl | 98.1 | 75.8 | 86.9 | 13.1 |
| Potentiated water | 10 μl | 140.1 | 106.2 | 123.2 | −23.2 |

Effect of the preparations and potentiated water on binding of standard ligand [$^3$H] pentazocine to human recombinant σ 1 receptor
Note:
% of specific binding in control = (specific binding during the test/specific binding in control) * 100%;
% of specific binding inhibition in control = 100% - (specific binding during the test/specific binding in control) * 100%).

The results reflecting inhibition above 50% represents significant effects of the tested compounds; inhibition from 25% to 50% confirms mild to moderate effects; inhibition less than 25% is considered to be insignificant effect of the tested compound and is within background level.

Therefore, this test model showed that the complex preparation of ULD of anti-S100+anti-eNOS is more efficient than its separate components (ULD of anti-S100 and ULD of anti-eNOS) in inhibiting the binding of standard radioligand [$^3$H]pentazocine to human recombinant σ1 receptor; ULD of anti-S100, transferred into the test basin, namely 10 μl, inhibit the binding of standard radioligand [3H]pentazocine to human recombinant al receptor, but the effect intensity is inferior to that of the complex preparation of ULD of anti-S100+anti-eNOS; ULD of anti-eNOS, transferred into the test well, namely 10 μl, had no effect on the binding of standard radioligand [3H]pentazocine to human recombinant σ1 receptor; potentiated water, transferred into the test basin, namely 10 μl or 20 μl, had no effect on the binding of standard radioligand [3H]pentazocine to human recombinant al receptor.

Example 2

Group 1—the active drug group was given 300 mg tablets impregnated with an aqueous-alcohol solutions (6 mg/tab) of activated-potentiated form of polyclonal rabbit antibodies to brain specific S-100 protein (anti-S-100), and to endothelial NO-synthase (anti-eNOS) in ultra low dose (ULD anti-S-100+ULD anti-eNOS), purified on antigen, obtained by super dilution of initial solution (with concentration of 2.5 mg/ml) in $100^{12}$, $100^{30}$, $100^{200}$ time, equivalent to mixture of centesimal homeopathic dilutions C12, C30, C200;

Group 2—the comparison group was given 300 mg tablets impregnated with an aqueous-alcohol solution (3 mg/tab) of activated-potentiated forms of polyclonal rabbit antibodies to brain-specific S-100 protein purified on antigen in ultra low dose (ULD anti-S100) obtained by super dilution of initial solution in $100^{12}$, $100^{30}$, $100^{50}$ times, of equivalent mixture homeopathic dilutions C12, C30, C50.

Group 3—the control group (placebo) was given of 300 mg tablets having excipients (lactose monohydrate—267 mg, microcrystal cellulose—30 mg, magnesium stearate—3 mg).

The effectiveness of the active drug ULD anti-S100+anti-eNOS in the treatment of patients with syndrome of attention deficit and hyperactivity disorder (ADHD) was conducted in comparative double blind placebo-controlled study in 146 children from 6 to 12 years old (mean age 9.3±0.24 years old) who were randomized into three groups depending on prescribed therapy. Within 12 weeks the patients of group No. 1 (n=46) received the composition ULD anti-S100+anti-eNOS, 2 tablets twice a day; the comparison group 2 members (n=50) received ULD anti-S100, 2 tablets twice a day; the control group 3 members (n=50) received 2 tablets twice a day. All the patients included in the study had clinically marked presentations of ADHD which was confirmed by high points on ADHD symptoms assessing scale (ADHDRS-IV-Home Version): 33.8±0.92 in group 1; 32.5±1.14 in group 2 and 33.6±0.91 in group 3. Most of the children were characterized by a moderate degree of severity of ADHD according to the CGI-ADHD-Severity questionnaire. The total score on this scale was 4.0±0.02 points in the group 1, 4.0±0.03 points in the group 2, and 4.0±0.00 points in the group 3. Thus, initially the patients of the three groups had comparable indicators of the severity of ADHD. According to the results of neurological, clinical—laboratory and instrumental examination at the time of enrollment to the study no abnormalities in any patient was detected. Over the 12 weeks of treatment, patients were seen six times by a doctor. During which the physician-researcher recorded the dynamics of intensity of clinical presentations of ADHD (total score on a scale ADHDRS-IV-Home Version) and disease severity (on the CGI-ADHD-Severity), supervised the prescriptions and administration of treatment and evaluated the safety of the treatment.

The analysis of the effectiveness of 12 weeks of therapy in the three groups showed a decrease of more than 25% from the initial total score on a scale ADHDRS-IV-Home Version in 75% (n=36) of children treated with the composition ULD anti-S100+anti-eNOS; in 66% (n=33) of patients treated with ULD anti-S100 and in 56% (n=28) of children receiving placebo. Differences of efficiency between the groups showing a more detailed assessment, taking into account the three-level grading of improvement of condition (reduction of total score on a scale ADHDRS-IV for <25%, 25-49.9% or ≥50% from the baseline), are presented in Table 2. Significant improvement with a reduction in total score on 50% or more from the baseline was noted in 52% of children in group 9 who were taking ULD anti-S100+anti-eNOS, and in 34% of children in group 2 who were taking ULD anti-S100 (vs. 8% of patients in group 3 with placebo).

The dynamics of reducing the symptoms of ADHD during the treatment period (the value of the total score on the scale ADHDRS-IV-Home Version on each of six visits) is presented in FIG. 1 and Table 3. Significant reduction (p<0.001) of clinical implications of ADHD in comparison with the initial state is already occurred after 2 weeks of therapy in all three groups of observation. Positive dynamics was more significant in patients of groups 9 and 2 as the significant differences were identified in them between total scores ADHDRS-IV-Home Version, not only in relation to the screening visit but when compared with the indexes of the group 3 with placebo. In subsequent weeks of treatment the efficacy of treatment with composition ULD anti-S100+anti-eNOS and monocomponent preparation ULD-S100 started to grow, the most significantly in the active drug group (p<0.05). The resulting decrease in total score on a scale ADHDRS-IV-Home Version in children of the group 9 with ULD anti-S100+anti-eNOS was 16.5 points, in patients of the group 2 with ULD anti-S100-12.4 points (compared to 6.3 points in the group 3 with placebo). As a result of 12-week of treatment the intensity of clinical implications of ADHD in children treated with the composition ULD anti-S100+anti-eNOS decreased by almost in half (−48.8%) and in patients treated with ULD anti-S100 more than in one-third (−38.2%) compared with the baseline.

The intake of composition ULD anti-S100+anti-eNOS or ULD anti-S100 influenced on both clusters of symptoms of ADHD which was confirmed by dynamics of assessments by two sections of the scale with ADHDRS-IV-Home Version (Table 3). Moreover, the treatment with the composition ULD anti-S100+anti-eNOS was significantly higher than the effectiveness of therapy with monopreparation ULD anti-S100 in the degree of influence on the intensity of implications and attention deficit and hyperactivity/impulsivity.

The positive therapeutic effect of the active drug ULD anti-S100+anti-eNOS and drug of comparison ULD-S100 was shown in evaluating of patients' treatment results on a scale of ADHD severity assessment (CGI-ADHR-Severity) (Table 4). Almost the fourth part of the patients in ULD anti-S100+anti-eNOS group the severity of disease was decreased from moderate to mild and even to minimal as confirmed by a decrease in mean value on a scale CGI-ADHR-Severity on 15% after 3 months of therapy (from 4.0±0.02 to 3.4±0.06; p<0.001). The effect of therapy with monopreparation ULD anti-S100 was slightly lower and indicated −10% on a scale CGI-ADHR-Severity over 3 months (vs. 5% in the placebo group). The safety analysis included data of all the patients participating in the study. During the whole period of monitoring there was both, well comparable to placebo, the tolerance of active drug ULD anti-S100+anti-eNOS and preparation of comparison ULD-S100. Adverse events were reported in one patient of the group with ULD anti-S100 (subside during the fourth week of the study headaches) and in one patient of the placebo group (sleepwalking during the second month of observation). These adverse events were not connected with the therapy. In addition, during the treatment the single cases of acute respiratory disease were observed which also are not associated with the therapy. All the patients of studied groups completed the treatment to schedule established by the study protocol; no early dropouts.

The absence of pathological changes according to physical examination of the patients and in the course of repeated analysis of laboratory parameters confirmed the safety of studied therapy.

According to the results of physical examination (heart rate, SBP, DBP, body temperature) in patients any pathological alterations during treatment were not registered. Differences in analyzing rates according to visits and in the compared groups did not reach the statistical significance and do not exceed the limits of physiologically-allowable deviations. High rates of adherence to therapy additionally evidenced as about effectiveness so as about the safety of studied preparations. By the end of the third month of treatment the adherence was 99.8±1.15% and 98.8±2.25% in the group 9 with ULD anti-S100+anti-eNOS and in the group 2 with ULD anti-S100 respectively (versus 74.6±2.54% in the group 3 with placebo).

Thus, the study demonstrated the efficacy and safety of the compositions ULD anti-S100+anti-eNOS and of monocomponent preparation ULD-S100 in the treatment of children with ADHD. The most pronounced therapeutic effect in the 12-week course was observed in complex drug (ULD anti-S100+anti-eNOS) which was manifested by positive dynamics of clinical symptoms in the majority (75%) of children. The composition ULD anti-S100+anti-eNOS had correcting influence to both of the clusters of symptoms of ADHD and as a result, the significant reduction of attention disorders and hyperactivity in patients with ADHD was noted.

TABLE 2

The dynamics of total score by the scale ADHDRS-IV-Home Version by the end of 12 weeks of therapy

| | The proportion of patients with decrease of total score by the scale ADHDRS-IV-Home Version | | |
|---|---|---|---|
| Group of patients | Less than 25.0% from baseline | on 25.0-49.9% from baseline | on 50.0% and more from baseline |
| ULD anti-S100 + anti-eNOS, n = 48 | 12 (25%) | 11 (23%) | 25 (52%) ## |
| ULD anti-S100, n = 50 | 17 (34%) | 16 (32%) | 17 (34%) ## |
| Placebo, n = 50 | 22 (44%) | 24 (48%) | 4 (8%) |

The difference is significant in comparison with the placebo group:
$p < 0.01$.

TABLE 3

The dynamics of evidence of clinical implications of ADHD by the scale ADHDRS-IV-Home Version

| | ULD anti-S100 + anti-eNOS, n = 48 | | ULD anti-S100, n = 50 | | Placebo, n = 50 | |
|---|---|---|---|---|---|---|
| Treatment stage | Value (M ± SE) | Δ from baseline | Value (M ± SE) | Δ from baseline | Value (M ± SE) | Δ from baseline |
| Total score | | | | | | |
| Screening | 33.8 ± 0.96 | | 32.5 ± 1.14 | | 33.6 ± 0.91 | |
| 2 weeks | 24.1 ± 0.97***# | −28.7% | 25.1 ± 1.03***# | −22.8% | 28.8 ± 1.26*** | −14.3% |
| 4 weeks | 22.6 ± 0.98***## | −33.1% | 22.7 ± 1.23***## | −30.2% | 29.9 ± 1.06*** | −11.0% |
| 6 weeks | 19.4 ± 0.95***## | −42.6% | 20.8 ± 1.06***## | −36.0% | 29.0 ± 1.25*** | −13.7% |
| 8 weeks | 18.9 ± 0.94***### | −44.1% | 20.9 ± 1.30***### | −35.7% | 27.6 ± 1.35*** | −17.9% |
| 12 weeks | 17.3 ± 0.96***###& | −48.8% | 20.1 ± 1.21***### | −38.2% | 27.3 ± 1.48*** | −18.8% |
| Attention disorders | | | | | | |
| Screening | 18.4 ± 0.55 | | 17.4 ± 0.57 | | 18.4 ± 0.43 | |
| 2 weeks | 12.8 ± 0.57***# | −30.4% | 13.7 ± 0.68***# | −21.3% | 16.1 ± 0.66*** | −12.5% |

TABLE 3-continued

The dynamics of evidence of clinical implications of ADHD by the scale ADHDRS-IV-Home Version

| Treatment stage | ULD anti-S100 + anti-eNOS, n = 48 | | ULD anti-S100, n = 50 | | Placebo, n = 50 | |
|---|---|---|---|---|---|---|
| | Value (M ± SE) | Δ from baseline | Value (M ± SE) | Δ from baseline | Value (M ± SE) | Δ from baseline |
| 4 weeks | 11.6 ± 0.56***### | −37.0% | 12.9 ± 0.79***### | −25.9% | 16.4 ± 0.57*** | −10.9% |
| 6 weeks | 10.7 ± 0.54***### | −41.8% | 11.9 ± 0.64***### | −31.6% | 16.0 ± 0.70*** | −13.0% |
| 8 weeks | 10.3 ± 0.53***### | −44.0% | 11.5 ± 0.70***### | −33.9% | 15.1 ± 0.76*** | −17.9% |
| 12 weeks | 9.7 ± 0.55***###& | −47.3% | 11.4 ± 0.68***## | −34.5% | 14.9 ± 0.78*** | −19.0% |
| Hyperactivity/impulsion | | | | | | |
| Screening | 15.4 ± 0.61 | | 15.1 ± 0.77 | | 15.2 ± 0.62 | |
| 2 weeks | 11.3 ± 0.63*** | −26.6% | 11.4 ± 0.61*** | −24.5% | 12.7 ± 0.74*** | −16.4% |
| 4 weeks | 11.0 ± 0.62***## | −28.6% | 9.8 ± 0.64***### | −35.1% | 13.5 ± 0.67** | −11.2% |
| 6 weeks | 8.7 ± 0.59***## | −43.5% | 8.9 ± 0.64***### | −41.1% | 12.9 ± 0.73** | −15.1% |
| 8 weeks | 8.6 ± 0.60***## | −44.2% | 9.5 ± 0.76***### | −37.1% | 12.5 ± 0.81*** | −17.8% |
| 12 weeks | 7.6 ± 0.57***###& | −50.6% | 8.7 ± 0.70***### | −42.4% | 12.5 ± 0.82*** | −17.8% |

Note.
The difference is significant in comparison with baseline parameter:
*$p < 0.05$,
**$p < 0.01$,
***$p < 0.001$.
The difference is significant in comparison with placebo group:
$p < 0.05$,
$p < 0.01$,
$p < 0.001$.
The difference is significant in comparison with the group of ULD anti-S100:
&$p < 0.05$.

TABLE 4

The dynamics of severity level of ADHD by the scale CGI-ADHD-Severity

| Parameter | ADHD Severity | |
|---|---|---|
| | M ± SE | Δ from baseline |
| ULD anti-S100 + anti-eNOS, n = 48 | | |
| Screening | 4.0 ± 0.02 | |
| 4 Weeks | 3.6 ± 0.02** | −10% |
| 12 Weeks | 3.4 ± 0.06*** | −15% |
| ULD anti-S100, n = 50 | | |
| Screening | 4.0 ± 0.03 | |
| 4 Weeks | 3.8 ± 0.06** | −5% |
| 12 Weeks | 3.6 ± 0.08*** | −10% |
| Placebo, n = 50 | | |
| Screening | 4.0 ± 0.01 | |
| 4 Weeks | 3.9 ± 0.05 | −2.5% |
| 12 Weeks | 3.8 ± 0.06*** | −2.5% |

The difference is significant in comparison with the baseline parameter:
**$p < 0.01$,
***$p < 0.001$.

The invention claimed is:

1. A method of treating attention deficit hyperactivity disorder, said method comprising administering to a patient in need thereof a combination pharmaceutical composition comprising a) an activated-potentiated form of an antibody to brain-specific protein S-100 and b) activated-potentiated form of antibodies to endothelial NO synthase.

2. The method of claim 1, wherein the activated-potentiated form of an antibody to brain-specific protein S-100 is to the entire bovine brain-specific protein S-100.

3. The method of claim 1, wherein the activated-potentiated form of an antibody to brain-specific protein S-100 is to brain-specific protein S-100 having SEQ ID NO: 9, SEQ ID NO: 10, SEQ ID NO: 11, or SEQ ID NO: 12.

4. The method of claim 1, wherein the activated-potentiated form of an antibody to endothelial NO synthase is to the entire bovine NO synthase.

5. The method of claim 1, wherein the activated-potentiated form of an antibody to endothelial NO synthase is to the entire human NO synthase.

6. The method of claim 1, wherein the activated-potentiated form of an antibody to brain-specific protein S-100 is a mixture of C12, C30, and C50 homeopathic dilutions and the activated-potentiated form of an antibody to endothelial NO synthase is a mixture of C12, C30, and C50 homeopathic dilutions.

7. The method of claim 1, wherein the activated-potentiated form of an antibody to brain-specific protein S-100 is a mixture of C12, C30, and C200 homeopathic dilutions and the activated-potentiated form of an antibody to endothelial NO synthase is a mixture of C12, C30, and C200 homeopathic dilutions.

8. The method of claim 1, wherein the activated-potentiated form of an antibody to endothelial NO synthase is a mixture of C12, C30, and C50 homeopathic dilutions impregnated onto a solid carrier and the activated-potentiated form of an antibody to brain-specific protein S-100 is a mixture of C12, C30, and C50 homeopathic dilutions impregnated onto the solid carrier.

9. The method of claim 1, wherein the activated-potentiated form of an antibody to endothelial NO synthase is a mixture of C12, C30, and C200 homeopathic dilutions impregnated onto a solid carrier and the activated-potentiated form of an antibody to brain-specific protein S-100 is a mixture of C12, C30, and C200 homeopathic dilutions impregnated onto the solid carrier.

10. The method of claim 1, wherein the antibody to brain-specific protein S-100 and the antibody to endothelial NO synthase is a monoclonal, polyclonal or natural antibody.

11. The method of claim 10, wherein the antibody to brain-specific protein S-100 and the antibody to endothelial NO synthase is a polyclonal antibody.

12. The method of claim 1, wherein a) the activated-potentiated form of an antibody to brain-specific protein S-100 and b) the activated-potentiated form of an antibody to endothelial NO synthase is prepared by successive centesimal dilutions coupled with shaking of every dilution.

13. The method of claim 1, wherein the combination pharmaceutical composition is administered in one to two unit dosages from once daily to four times daily.

14. The method of claim 13, wherein the combination pharmaceutical composition is administered in one to two unit dosages twice daily.

15. The method of claim 1 wherein the step of administering to the patient the combination pharmaceutical composition results in the reduction of the symptoms of attention deficit hyperactivity disorder as measured by the ADHDRS-IV Home Version test.

16. The method of claim 1 wherein the step of administering to the patient the combination pharmaceutical composition results in the reduction of the symptoms of attention deficit hyperactivity disorder as measured by the CGI-ADHD severity test.

17. The method of claim 1, wherein said patient is a child under the age of 12 years.

18. The method of claim 1, wherein said patient is an adult.

19. A method of treating attention deficit disorder, said method comprising administering to a patient in need thereof a combination pharmaceutical composition comprising a) an activated-potentiated form of an antibody to brain-specific protein S-100 and b) activated-potentiated form of antibodies to endothelial NO synthase.

20. The method of claim 19, wherein the activated-potentiated form of an antibody to brain-specific protein S-100 is to the entire bovine brain-specific protein S-100.

21. The method of claim 19, wherein the activated-potentiated form of an antibody to brain-specific protein S-100 is to brain-specific protein S-100 having SEQ ID NO: 9, SEQ ID NO: 10, SEQ ID NO: 11, or SEQ ID NO: 12.

22. The method of claim 19, wherein the activated-potentiated form of an antibody to endothelial NO synthase is to the entire bovine NO synthase.

23. The method of claim 19, wherein the activated-potentiated form of an antibody to endothelial NO synthase is to the entire human NO synthase.

24. The method of claim 19, wherein the activated-potentiated form of an antibody to brain-specific protein S-100 is a mixture of C12, C30, and C50 homeopathic dilutions and the activated-potentiated form of an antibody to endothelial NO synthase is a mixture of C12, C30, and C50 homeopathic dilutions.

25. The method of claim 19, wherein the activated-potentiated form of an antibody to brain-specific protein S-100 is a mixture of C12, C30, and C200 homeopathic dilutions and the activated-potentiated form of an antibody to endothelial NO synthase is a mixture of C12, C30, and C200 homeopathic dilutions.

26. The method of claim 19, wherein the activated-potentiated form of an antibody to endothelial NO synthase is a mixture of C12, C30, and C50 homeopathic dilutions impregnated onto a solid carrier and the activated-potentiated form of an antibody to brain-specific protein S-100 is a mixture of C12, C30, and C50 homeopathic dilutions impregnated onto the solid carrier.

27. The method of claim 19, wherein the activated-potentiated form of an antibody to endothelial NO synthase is a mixture of C12, C30, and C200 homeopathic dilutions impregnated onto a solid carrier and the activated-potentiated form of an antibody to brain-specific protein S-100 is a mixture of C12, C30, and C200 homeopathic dilutions impregnated onto the solid carrier.

28. The method of claim 19, wherein a) the activated-potentiated form of an antibody to brain-specific protein S-100 and b) the activated-potentiated form of an antibody to endothelial NO synthase is a monoclonal, polyclonal or natural antibody.

29. The method of claim 19, wherein the antibody to brain-specific protein S-100 and the antibody to endothelial NO synthase is a polyclonal antibody.

30. The method of claim 19, wherein a) the activated-potentiated form of an antibody to brain-specific protein S-100 and b) the activated-potentiated form of an antibody to endothelial NO synthase is prepared by successive centesimal dilutions coupled with shaking of every dilution.

31. The method of claim 19, wherein the combination pharmaceutical composition is administered in one to two unit dosages from once daily to four times daily.

32. The method of claim 31, wherein the combination pharmaceutical composition is administered in one to two unit dosages twice daily.

\* \* \* \* \*

SEQUENCE LISTING

<160> NUMBER OF SEQ ID NOS: 12

<210> SEQ ID NO 1
<211> LENGTH: 1205
<212> TYPE: PRT
<213> ORGANISM: Bos taurus
<220> FEATURE:
<221> NAME/KEY: SOURCE
<222> LOCATION: 1..1205
<223> OTHER INFORMATION: /mol_type="protein"
      /organism="Bos taurus"

<400> SEQUENCE: 1

```
Met Gly Asn Leu Lys Ser Val Gly Gln Glu Pro Gly Pro Pro Cys Gly
1               5                   10                  15

Leu Gly Leu Gly Leu Gly Leu Gly Cys Gly Lys Gln Gly Pro Ala
            20                  25                  30

Ser Pro Ala Pro Glu Pro Ser Arg Ala Pro Ala Pro Thr Pro His
        35                  40                  45

Ala Pro Asp His Ser Pro Ala Pro Asn Ser Pro Thr Leu Thr Arg Pro
 50                  55                  60

Pro Glu Gly Pro Lys Phe Pro Arg Val Lys Asn Trp Glu Leu Gly Ser
65                  70                  75                  80

Ile Thr Tyr Asp Thr Leu Cys Ala Gln Ser Gln Gln Asp Gly Pro Cys
                85                  90                  95

Thr Pro Arg Cys Cys Leu Gly Ser Leu Val Leu Pro Arg Lys Leu Gln
            100                 105                 110

Thr Arg Pro Ser Pro Gly Pro Pro Ala Glu Gln Leu Leu Ser Gln
        115                 120                 125

Ala Arg Asp Phe Ile Asn Gln Tyr Tyr Ser Ser Ile Lys Arg Ser Gly
        130                 135                 140

Ser Gln Ala His Glu Glu Arg Leu Gln Glu Val Glu Ala Glu Val Ala
145                 150                 155                 160

Ser Thr Gly Thr Tyr His Leu Arg Glu Ser Glu Leu Val Phe Gly Ala
                165                 170                 175

Lys Gln Ala Trp Arg Asn Ala Pro Arg Cys Val Gly Arg Ile Gln Trp
            180                 185                 190

Gly Lys Leu Gln Val Phe Asp Ala Arg Asp Cys Ser Ser Ala Gln Glu
        195                 200                 205

Met Phe Thr Tyr Ile Cys Asn His Ile Lys Tyr Ala Thr Asn Arg Gly
210                 215                 220

Asn Leu Arg Ser Ala Ile Thr Val Phe Pro Gln Arg Ala Pro Gly Arg
225                 230                 235                 240

Gly Asp Phe Arg Ile Trp Asn Ser Gln Leu Val Arg Tyr Ala Gly Tyr
                245                 250                 255

Arg Gln Gln Asp Gly Ser Val Arg Gly Asp Pro Ala Asn Val Glu Ile
            260                 265                 270

Thr Glu Leu Cys Ile Gln His Gly Trp Thr Pro Gly Asn Gly Arg Phe
        275                 280                 285

Asp Val Leu Pro Leu Leu Leu Gln Ala Pro Asp Glu Ala Pro Glu Leu
    290                 295                 300

Phe Val Leu Pro Pro Glu Leu Val Leu Glu Val Pro Leu Glu His Pro
305                 310                 315                 320

Thr Leu Glu Trp Phe Ala Ala Leu Gly Leu Arg Trp Tyr Ala Leu Pro
                325                 330                 335

Ala Val Ser Asn Met Leu Leu Glu Ile Gly Gly Leu Glu Phe Ser Ala
```

```
                    340                 345                 350
Ala Pro Phe Ser Gly Trp Tyr Met Ser Thr Glu Ile Gly Thr Arg Asn
            355                 360                 365

Leu Cys Asp Pro His Arg Tyr Asn Ile Leu Glu Asp Val Ala Val Cys
    370                 375                 380

Met Asp Leu Asp Thr Arg Thr Thr Ser Ser Leu Trp Lys Asp Lys Ala
385                 390                 395                 400

Ala Val Glu Ile Asn Leu Ala Val Leu His Ser Phe Gln Leu Ala Lys
                405                 410                 415

Val Thr Ile Val Asp His His Ala Ala Thr Val Ser Phe Met Lys His
                420                 425                 430

Leu Asp Asn Glu Gln Lys Ala Arg Gly Gly Cys Pro Ala Asp Trp Ala
            435                 440                 445

Trp Ile Val Pro Pro Ile Ser Gly Ser Leu Thr Pro Val Phe His Gln
        450                 455                 460

Glu Met Val Asn Tyr Ile Leu Ser Pro Ala Phe Arg Tyr Gln Pro Asp
465                 470                 475                 480

Pro Trp Lys Gly Ser Ala Thr Lys Gly Ala Gly Ile Thr Arg Lys Lys
                485                 490                 495

Thr Phe Lys Glu Val Ala Asn Ala Val Lys Ile Ser Ala Ser Leu Met
                500                 505                 510

Gly Thr Leu Met Ala Lys Arg Val Lys Ala Thr Ile Leu Tyr Ala Ser
        515                 520                 525

Glu Thr Gly Arg Ala Gln Ser Tyr Ala Gln Gln Leu Gly Arg Leu Phe
        530                 535                 540

Arg Lys Ala Phe Asp Pro Arg Val Leu Cys Met Asp Glu Tyr Asp Val
545                 550                 555                 560

Val Ser Leu Glu His Glu Ala Leu Val Leu Val Val Thr Ser Thr Phe
                565                 570                 575

Gly Asn Gly Asp Pro Pro Glu Asn Gly Glu Ser Phe Ala Ala Ala Leu
                580                 585                 590

Met Glu Met Ser Gly Pro Tyr Asn Ser Ser Pro Arg Pro Glu Gln His
        595                 600                 605

Lys Ser Tyr Lys Ile Arg Phe Asn Ser Val Ser Cys Ser Asp Pro Leu
    610                 615                 620

Val Ser Ser Trp Arg Arg Lys Arg Lys Glu Ser Ser Asn Thr Asp Ser
625                 630                 635                 640

Ala Gly Ala Leu Gly Thr Leu Arg Phe Cys Val Phe Gly Leu Gly Ser
                645                 650                 655

Arg Ala Tyr Pro His Phe Cys Ala Phe Ala Arg Ala Val Asp Thr Arg
                660                 665                 670

Leu Glu Glu Leu Gly Gly Glu Arg Leu Leu Gln Leu Gly Gln Gly Asp
        675                 680                 685

Glu Leu Cys Gly Gln Glu Glu Ala Phe Arg Gly Trp Ala Lys Ala Ala
        690                 695                 700

Phe Gln Ala Ser Cys Glu Thr Phe Cys Val Gly Glu Glu Ala Lys Ala
705                 710                 715                 720

Ala Ala Gln Asp Ile Phe Ser Pro Lys Arg Ser Trp Lys Arg Gln Arg
                725                 730                 735

Tyr Arg Leu Ser Thr Gln Ala Glu Gly Leu Gln Leu Leu Pro Gly Leu
            740                 745                 750

Ile His Val His Arg Arg Lys Met Phe Gln Ala Thr Val Leu Ser Val
        755                 760                 765
```

```
Glu Asn Leu Gln Ser Ser Lys Ser Thr Arg Ala Thr Ile Leu Val Arg
    770             775             780

Leu Asp Thr Ala Gly Gln Glu Gly Leu Gln Tyr Gln Pro Gly Asp His
785             790             795             800

Ile Gly Ile Cys Pro Pro Asn Arg Pro Gly Leu Val Glu Ala Leu Leu
                805             810             815

Ser Arg Val Glu Asp Pro Pro Pro Thr Glu Ser Val Ala Val Glu
            820             825             830

Gln Leu Glu Lys Gly Ser Pro Gly Gly Pro Pro Ser Trp Val Arg
            835             840             845

Asp Pro Arg Leu Pro Pro Cys Thr Leu Arg Gln Ala Leu Thr Phe Phe
850             855             860

Leu Asp Ile Thr Ser Pro Pro Ser Pro Arg Leu Leu Arg Leu Leu Ser
865             870             875             880

Thr Leu Ala Glu Glu Pro Ser Glu Gln Gln Glu Leu Glu Thr Leu Ser
            885             890             895

Gln Asp Pro Arg Arg Tyr Glu Glu Trp Lys Trp Phe Arg Cys Pro Thr
            900             905             910

Leu Leu Glu Val Leu Gln Phe Pro Ser Val Ala Leu Pro Ala Pro
            915             920             925

Leu Leu Leu Thr Gln Leu Pro Leu Leu Gln Pro Arg Tyr Tyr Ser Val
            930             935             940

Ser Ser Ala Pro Asn Ala His Pro Gly Glu Val His Leu Thr Val Ala
945             950             955             960

Val Leu Ala Tyr Arg Thr Gln Asp Gly Leu Gly Pro Leu His Tyr Gly
            965             970             975

Val Cys Ser Thr Trp Leu Ser Gln Leu Lys Thr Gly Asp Pro Val Pro
            980             985             990

Cys Phe Ile Arg Gly Ala Pro Ser Phe Arg Leu Pro Pro Asp Pro Tyr
            995             1000            1005

Val Pro Cys Ile Leu Val Gly Pro Gly Thr Gly Ile Ala Pro Phe Arg
    1010            1015            1020

Gly Phe Trp Gln Glu Arg Leu His Asp Ile Glu Ser Lys Gly Leu Gln
1025            1030            1035            1040

Pro Ala Pro Met Thr Leu Val Phe Gly Cys Arg Cys Ser Gln Leu Asp
                1045            1050            1055

His Leu Tyr Arg Asp Glu Val Gln Asp Ala Gln Glu Arg Gly Val Phe
            1060            1065            1070

Gly Arg Val Leu Thr Ala Phe Ser Arg Glu Pro Asp Ser Pro Lys Thr
            1075            1080            1085

Tyr Val Gln Asp Ile Leu Arg Thr Glu Leu Ala Ala Glu Val His Arg
            1090            1095            1100

Val Leu Cys Leu Glu Arg Gly His Met Phe Val Cys Gly Asp Val Thr
1105            1110            1115            1120

Met Ala Thr Ser Val Leu Gln Thr Val Gln Arg Ile Leu Ala Thr Glu
                1125            1130            1135

Gly Asp Met Glu Leu Asp Glu Ala Gly Asp Val Ile Gly Val Leu Arg
            1140            1145            1150

Asp Gln Gln Arg Tyr His Glu Asp Ile Phe Gly Leu Thr Leu Arg Thr
            1155            1160            1165

Gln Glu Val Thr Ser Arg Ile Arg Thr Gln Ser Phe Ser Leu Gln Glu
            1170            1175            1180
```

Arg His Leu Arg Gly Ala Val Pro Trp Ala Phe Asp Pro Pro Gly Pro
1185                1190                1195                1200

Asp Thr Pro Gly Pro
            1205

<210> SEQ ID NO 2
<211> LENGTH: 1203
<212> TYPE: PRT
<213> ORGANISM: Homo sapiens
<220> FEATURE:
<221> NAME/KEY: SOURCE
<222> LOCATION: 1..1203
<223> OTHER INFORMATION: /mol_type="protein"
      /organism="Homo sapiens"

<400> SEQUENCE: 2

Met Gly Asn Leu Lys Ser Val Ala Gln Glu Pro Gly Pro Pro Cys Gly
1               5                   10                  15

Leu Gly Leu Gly Leu Gly Leu Gly Leu Cys Gly Lys Gln Gly Pro Ala
            20                  25                  30

Thr Pro Ala Pro Glu Pro Ser Arg Ala Pro Ala Ser Leu Leu Pro Pro
        35                  40                  45

Ala Pro Glu His Ser Pro Ser Ser Pro Leu Thr Gln Pro Pro Glu
50                  55                  60

Gly Pro Lys Phe Pro Arg Val Lys Asn Trp Glu Val Gly Ser Ile Thr
65              70                  75                  80

Tyr Asp Thr Leu Ser Ala Gln Ala Gln Asp Gly Pro Cys Thr Pro
                85                  90                  95

Arg Arg Cys Leu Gly Ser Leu Val Phe Pro Arg Lys Leu Gln Gly Arg
                100                 105                 110

Pro Ser Pro Gly Pro Pro Ala Pro Glu Gln Leu Leu Ser Gln Ala Arg
            115                 120                 125

Asp Phe Ile Asn Gln Tyr Tyr Ser Ser Ile Lys Arg Ser Gly Ser Gln
130                 135                 140

Ala His Glu Gln Arg Leu Gln Glu Val Glu Ala Glu Val Ala Ala Thr
145                 150                 155                 160

Gly Thr Tyr Gln Leu Arg Glu Ser Glu Leu Val Phe Gly Ala Lys Gln
                165                 170                 175

Ala Trp Arg Asn Ala Pro Arg Cys Val Gly Arg Ile Gln Trp Gly Lys
            180                 185                 190

Leu Gln Val Phe Asp Ala Arg Asp Cys Arg Ser Ala Gln Glu Met Phe
        195                 200                 205

Thr Tyr Ile Cys Asn His Ile Lys Tyr Ala Thr Asn Arg Gly Asn Leu
210                 215                 220

Arg Ser Ala Ile Thr Val Phe Pro Gln Arg Cys Pro Gly Arg Gly Asp
225                 230                 235                 240

Phe Arg Ile Trp Asn Ser Gln Leu Val Arg Tyr Ala Gly Tyr Arg Gln
                245                 250                 255

Gln Asp Gly Ser Val Arg Gly Asp Pro Ala Asn Val Glu Ile Thr Glu
            260                 265                 270

Leu Cys Ile Gln His Gly Trp Thr Pro Gly Asn Gly Arg Phe Asp Val
        275                 280                 285

Leu Pro Leu Leu Leu Gln Ala Pro Asp Glu Pro Pro Glu Leu Phe Leu
290                 295                 300

Leu Pro Pro Glu Leu Val Leu Glu Val Pro Leu Glu His Pro Thr Leu
305                 310                 315                 320

```
Glu Trp Phe Ala Ala Leu Gly Leu Arg Trp Tyr Ala Leu Pro Ala Val
                325                 330                 335

Ser Asn Met Leu Leu Glu Ile Gly Gly Leu Glu Phe Pro Ala Ala Pro
            340                 345                 350

Phe Ser Gly Trp Tyr Met Ser Thr Glu Ile Gly Thr Arg Asn Leu Cys
        355                 360                 365

Asp Pro His Arg Tyr Asn Ile Leu Glu Asp Val Ala Val Cys Met Asp
    370                 375                 380

Leu Asp Thr Arg Thr Thr Ser Ser Leu Trp Lys Asp Lys Ala Ala Val
385                 390                 395                 400

Glu Ile Asn Val Ala Val Leu His Ser Tyr Gln Leu Ala Lys Val Thr
                405                 410                 415

Ile Val Asp His His Ala Ala Thr Ala Ser Phe Met Lys His Leu Glu
            420                 425                 430

Asn Glu Gln Lys Ala Arg Gly Gly Cys Pro Ala Asp Trp Ala Trp Ile
        435                 440                 445

Val Pro Pro Ile Ser Gly Ser Leu Thr Pro Val Phe His Gln Glu Met
    450                 455                 460

Val Asn Tyr Phe Leu Ser Pro Ala Phe Arg Tyr Gln Pro Asp Pro Trp
465                 470                 475                 480

Lys Gly Ser Ala Ala Lys Gly Thr Gly Ile Thr Arg Lys Lys Thr Phe
                485                 490                 495

Lys Glu Val Ala Asn Ala Val Lys Ile Ser Ala Ser Leu Met Gly Thr
            500                 505                 510

Val Met Ala Lys Arg Val Lys Ala Thr Ile Leu Tyr Gly Ser Glu Thr
        515                 520                 525

Gly Arg Ala Gln Ser Tyr Ala Gln Gln Leu Gly Arg Leu Phe Arg Lys
    530                 535                 540

Ala Phe Asp Pro Arg Val Leu Cys Met Asp Glu Tyr Asp Val Val Ser
545                 550                 555                 560

Leu Glu His Glu Thr Leu Val Leu Val Val Thr Ser Thr Phe Gly Asn
                565                 570                 575

Gly Asp Pro Pro Glu Asn Gly Glu Ser Phe Ala Ala Ala Leu Met Glu
            580                 585                 590

Met Ser Gly Pro Tyr Asn Ser Ser Pro Arg Pro Glu Gln His Lys Ser
        595                 600                 605

Tyr Lys Ile Arg Phe Asn Ser Ile Ser Cys Ser Asp Pro Leu Val Ser
    610                 615                 620

Ser Trp Arg Arg Lys Arg Lys Glu Ser Ser Asn Thr Asp Ser Ala Gly
625                 630                 635                 640

Ala Leu Gly Thr Leu Arg Phe Cys Val Phe Gly Leu Gly Ser Arg Ala
                645                 650                 655

Tyr Pro His Phe Cys Ala Phe Ala Arg Ala Val Asp Thr Arg Leu Glu
            660                 665                 670

Glu Leu Gly Gly Glu Arg Leu Leu Gln Leu Gly Gln Gly Asp Glu Leu
        675                 680                 685

Cys Gly Gln Glu Glu Ala Phe Arg Gly Trp Ala Gln Ala Ala Phe Gln
    690                 695                 700

Ala Ala Cys Glu Thr Phe Cys Val Gly Glu Asp Ala Lys Ala Ala Ala
705                 710                 715                 720

Arg Asp Ile Phe Ser Pro Lys Arg Ser Trp Lys Arg Gln Arg Tyr Arg
                725                 730                 735

Leu Ser Ala Gln Ala Glu Gly Leu Gln Leu Leu Pro Gly Leu Ile His
```

```
                740              745              750
Val His Arg Arg Lys Met Phe Gln Ala Thr Ile Arg Ser Val Glu Asn
            755              760              765

Leu Gln Ser Ser Lys Ser Thr Arg Ala Thr Ile Leu Val Arg Leu Asp
            770              775              780

Thr Gly Gly Gln Glu Gly Leu Gln Tyr Gln Pro Gly Asp His Ile Gly
785              790              795              800

Val Cys Pro Pro Asn Arg Pro Gly Leu Val Glu Ala Leu Leu Ser Arg
            805              810              815

Val Glu Asp Pro Pro Ala Pro Thr Glu Pro Val Ala Val Glu Gln Leu
            820              825              830

Glu Lys Gly Ser Pro Gly Gly Pro Pro Gly Trp Val Arg Asp Pro
            835              840              845

Arg Leu Pro Pro Cys Thr Leu Arg Gln Ala Leu Thr Phe Phe Leu Asp
            850              855              860

Ile Thr Ser Pro Pro Ser Pro Gln Leu Leu Arg Leu Leu Ser Thr Leu
865              870              875              880

Ala Glu Glu Pro Arg Glu Gln Gln Glu Leu Glu Ala Leu Ser Gln Asp
            885              890              895

Pro Arg Arg Tyr Glu Glu Trp Lys Trp Phe Arg Cys Pro Thr Leu Leu
            900              905              910

Glu Val Leu Glu Gln Phe Pro Ser Val Ala Leu Pro Ala Pro Leu Leu
            915              920              925

Leu Thr Gln Leu Pro Leu Leu Gln Pro Arg Tyr Tyr Ser Val Ser Ser
            930              935              940

Ala Pro Ser Thr His Pro Gly Glu Ile His Leu Thr Val Ala Val Leu
945              950              955              960

Ala Tyr Arg Thr Gln Asp Gly Leu Gly Pro Leu His Tyr Gly Val Cys
            965              970              975

Ser Thr Trp Leu Ser Gln Leu Lys Pro Gly Asp Pro Val Pro Cys Phe
            980              985              990

Ile Arg Gly Ala Pro Ser Phe Arg Leu Pro Pro Asp Pro Ser Leu Pro
            995              1000             1005

Cys Ile Leu Val Gly Pro Gly Thr Gly Ile Ala Pro Phe Arg Gly Phe
            1010             1015             1020

Trp Gln Glu Arg Leu His Asp Ile Glu Ser Lys Gly Leu Gln Pro Thr
1025             1030             1035             1040

Pro Met Thr Leu Val Phe Gly Cys Arg Cys Ser Gln Leu Asp His Leu
                 1045             1050             1055

Tyr Arg Asp Glu Val Gln Asn Ala Gln Gln Arg Gly Val Phe Gly Arg
            1060             1065             1070

Val Leu Thr Ala Phe Ser Arg Glu Pro Asp Asn Pro Lys Thr Tyr Val
            1075             1080             1085

Gln Asp Ile Leu Arg Thr Glu Leu Ala Ala Glu Val His Arg Val Leu
            1090             1095             1100

Cys Leu Glu Arg Gly His Met Phe Val Cys Gly Asp Val Thr Met Ala
1105             1110             1115             1120

Thr Asn Val Leu Gln Thr Val Gln Arg Ile Leu Ala Thr Glu Gly Asp
            1125             1130             1135

Met Glu Leu Asp Glu Ala Gly Asp Val Ile Gly Val Leu Arg Asp Gln
            1140             1145             1150

Gln Arg Tyr His Glu Asp Ile Phe Gly Leu Thr Leu Arg Thr Gln Glu
            1155             1160             1165
```

Val Thr Ser Arg Ile Arg Thr Gln Ser Phe Ser Leu Gln Glu Arg Gln
        1170                1175                1180

Leu Arg Gly Ala Val Pro Trp Ala Phe Asp Pro Pro Gly Ser Asp Thr
1185                1190                1195                1200

Asn Ser Pro

<210> SEQ ID NO 3
<211> LENGTH: 4
<212> TYPE: PRT
<213> ORGANISM: Bos taurus
<220> FEATURE:
<221> NAME/KEY: SOURCE
<222> LOCATION: 1..4
<223> OTHER INFORMATION: /mol_type="protein"
      /organism="Bos taurus"

<400> SEQUENCE: 3

Pro Trp Ala Phe
1

<210> SEQ ID NO 4
<211> LENGTH: 4
<212> TYPE: PRT
<213> ORGANISM: Bos taurus
<220> FEATURE:
<221> NAME/KEY: SOURCE
<222> LOCATION: 1..4
<223> OTHER INFORMATION: /mol_type="protein"
      /organism="Bos taurus"

<400> SEQUENCE: 4

Gly Ala Val Pro
1

<210> SEQ ID NO 5
<211> LENGTH: 21
<212> TYPE: PRT
<213> ORGANISM: Bos taurus
<220> FEATURE:
<221> NAME/KEY: SOURCE
<222> LOCATION: 1..21
<223> OTHER INFORMATION: /mol_type="protein"
      /organism="Bos taurus"

<400> SEQUENCE: 5

Arg His Leu Arg Gly Ala Val Pro Trp Ala Phe Asp Pro Pro Gly Pro
1               5                   10                  15

Asp Thr Pro Gly Pro
            20

<210> SEQ ID NO 6
<211> LENGTH: 12
<212> TYPE: PRT
<213> ORGANISM: Bos taurus
<220> FEATURE:
<221> NAME/KEY: SOURCE
<222> LOCATION: 1..12
<223> OTHER INFORMATION: /mol_type="protein"
      /organism="Bos taurus"

<400> SEQUENCE: 6

Ala Phe Asp Pro Pro Gly Pro Asp Thr Pro Gly Pro
1               5                   10

<210> SEQ ID NO 7
<211> LENGTH: 11

```
<212> TYPE: PRT
<213> ORGANISM: Bos taurus
<220> FEATURE:
<221> NAME/KEY: SOURCE
<222> LOCATION: 1..11
<223> OTHER INFORMATION: /mol_type="protein"
      /organism="Bos taurus"

<400> SEQUENCE: 7

His Leu Arg Gly Ala Val Pro Trp Ala Phe Asp
1               5                   10

<210> SEQ ID NO 8
<211> LENGTH: 20
<212> TYPE: PRT
<213> ORGANISM: Bos taurus
<220> FEATURE:
<221> NAME/KEY: SOURCE
<222> LOCATION: 1..20
<223> OTHER INFORMATION: /mol_type="protein"
      /organism="Bos taurus"

<400> SEQUENCE: 8

His Leu Arg Gly Ala Val Pro Trp Ala Phe Asp Pro Pro Gly Pro Asp
1               5                   10                  15

Thr Pro Gly Pro
            20

<210> SEQ ID NO 9
<211> LENGTH: 92
<212> TYPE: PRT
<213> ORGANISM: Bos taurus
<220> FEATURE:
<221> NAME/KEY: SOURCE
<222> LOCATION: 1..92
<223> OTHER INFORMATION: /mol_type="protein"
      /organism="Bos taurus"

<400> SEQUENCE: 9

Met Ser Glu Leu Glu Lys Ala Val Val Ala Leu Ile Asp Val Phe His
1               5                   10                  15

Gln Tyr Ser Gly Arg Glu Gly Asp Lys His Lys Leu Lys Lys Ser Glu
                20                  25                  30

Leu Lys Glu Leu Ile Asn Asn Glu Leu Ser His Phe Leu Glu Glu Ile
            35                  40                  45

Lys Glu Gln Glu Val Val Asp Lys Val Met Glu Thr Leu Asp Ser Asp
        50                  55                  60

Gly Asp Gly Glu Cys Asp Phe Gln Glu Phe Met Ala Phe Val Ala Met
65                  70                  75                  80

Ile Thr Thr Ala Cys His Glu Phe Phe Glu His Glu
                85                  90

<210> SEQ ID NO 10
<211> LENGTH: 92
<212> TYPE: PRT
<213> ORGANISM: Homo sapiens
<220> FEATURE:
<221> NAME/KEY: SOURCE
<222> LOCATION: 1..92
<223> OTHER INFORMATION: /mol_type="protein"
      /organism="Homo sapiens"

<400> SEQUENCE: 10

Met Ser Glu Leu Glu Lys Ala Met Val Ala Leu Ile Asp Val Phe His
1               5                   10                  15
```

```
Gln Tyr Ser Gly Arg Glu Gly Asp Lys His Lys Leu Lys Lys Ser Glu
                20                  25                  30

Leu Lys Glu Leu Ile Asn Asn Glu Leu Ser His Phe Leu Glu Ile
            35                  40                  45

Lys Glu Gln Glu Val Val Asp Lys Val Met Glu Thr Leu Asp Asn Asp
 50                  55                  60

Gly Asp Gly Glu Cys Asp Phe Gln Glu Phe Met Ala Phe Val Ala Met
 65                  70                  75                  80

Val Thr Thr Ala Cys His Glu Phe Phe Glu His Glu
                85                  90

<210> SEQ ID NO 11
<211> LENGTH: 94
<212> TYPE: PRT
<213> ORGANISM: Bos taurus
<220> FEATURE:
<221> NAME/KEY: SOURCE
<222> LOCATION: 1..94
<223> OTHER INFORMATION: /mol_type="protein"
      /organism="Bos taurus"

<400> SEQUENCE: 11

Met Gly Ser Glu Leu Glu Thr Ala Met Glu Thr Leu Ile Asn Val Phe
 1               5                  10                  15

His Ala His Ser Gly Lys Glu Gly Asp Lys Tyr Lys Leu Ser Lys Lys
                20                  25                  30

Glu Leu Lys Glu Leu Leu Gln Thr Glu Leu Ser Gly Phe Leu Asp Ala
            35                  40                  45

Gln Lys Asp Val Asp Ala Val Asp Lys Val Met Lys Glu Leu Asp Glu
 50                  55                  60

Asn Gly Asp Gly Glu Val Asp Phe Gln Glu Tyr Val Val Leu Val Ala
 65                  70                  75                  80

Ala Leu Thr Val Ala Cys Asn Asn Phe Phe Trp Glu Asn Ser
                85                  90

<210> SEQ ID NO 12
<211> LENGTH: 94
<212> TYPE: PRT
<213> ORGANISM: Bos taurus
<220> FEATURE:
<221> NAME/KEY: SOURCE
<222> LOCATION: 1..94
<223> OTHER INFORMATION: /mol_type="protein"
      /organism="Bos taurus"

<400> SEQUENCE: 12

Met Gly Ser Glu Leu Glu Thr Ala Met Glu Thr Leu Ile Asn Val Phe
 1               5                  10                  15

His Ala His Ser Gly Lys Glu Gly Asp Lys Tyr Lys Leu Ser Lys Lys
                20                  25                  30

Glu Leu Lys Glu Leu Leu Gln Thr Glu Leu Ser Gly Phe Leu Asp Ala
            35                  40                  45

Gln Lys Asp Ala Asp Ala Val Asp Lys Val Met Lys Glu Leu Asp Glu
 50                  55                  60

Asn Gly Asp Gly Glu Val Asp Phe Gln Glu Tyr Val Val Leu Val Ala
 65                  70                  75                  80

Ala Leu Thr Val Ala Cys Asn Asn Phe Phe Trp Glu Asn Ser
                85                  90
```